US012767640B2

(12) United States Patent
Kramer et al.

(10) Patent No.: US 12,767,640 B2
(45) **Date of Patent: *Oct. 20, 2026**

(54) AMINO ACID COMPOSITIONS

(71) Applicant: ThermoLife International, LLC, Signal Hill, CA (US)

(72) Inventors: Ronald Kramer, Signal Hill, CA (US); Alexandros Nikolaidis, Nea Kallikratia (GR)

(73) Assignee: ThermoLife International, LLC, Signal, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/556,424

(22) Filed: Mar. 4, 2026

(65) Prior Publication Data

US 2026/0193191 A1 Jul. 9, 2026

Related U.S. Application Data

(60) Continuation of application No. 19/030,516, filed on Jan. 17, 2025, now Pat. No. 12,577,210, which is a continuation of application No. 17/522,680, filed on Nov. 9, 2021, now Pat. No. 12,227,483, which is a division of application No. 14/621,738, filed on Feb. 13, 2015, now Pat. No. 11,166,979, which is a continuation of application No. 13/920,066, filed on Jun. 17, 2013, now Pat. No. 8,957,100, which is a continuation of application No. 13/038,615, filed on Mar. 2, 2011, now Pat. No. 8,466,187, which is a continuation-in-part of application No. 12/336,938, filed on Dec. 17, 2008, now Pat. No. 8,034,836, which is a continuation of application No. 11/950,273, filed on Dec. 4, 2007, now Pat. No. 7,777,074.

(60) Provisional application No. 60/973,229, filed on Sep. 18, 2007.

(51) Int. Cl.

| | |
|---|---|
| ***C07C 229/08*** | (2006.01) |
| ***A61K 31/185*** | (2006.01) |
| ***A61K 31/197*** | (2006.01) |
| ***A61K 31/198*** | (2006.01) |
| ***A61K 31/205*** | (2006.01) |
| ***A61K 31/221*** | (2006.01) |
| ***A61K 31/401*** | (2006.01) |
| ***A61K 31/4172*** | (2006.01) |
| ***A61K 33/00*** | (2006.01) |
| ***C07C 229/24*** | (2006.01) |
| ***C07C 229/26*** | (2006.01) |
| ***C07C 237/06*** | (2006.01) |
| ***C07C 275/16*** | (2006.01) |
| ***C07C 279/02*** | (2006.01) |
| ***C07C 323/58*** | (2006.01) |
| ***C07D 207/16*** | (2006.01) |
| ***C07D 233/64*** | (2006.01) |

(52) U.S. Cl.

CPC .......... *C07D 233/64* (2013.01); *A61K 31/185* (2013.01); *A61K 31/197* (2013.01); *A61K 31/198* (2013.01); *A61K 31/205* (2013.01); *A61K 31/221* (2013.01); *A61K 31/401* (2013.01); *A61K 31/4172* (2013.01); *A61K 33/00* (2013.01); *C07C 229/08* (2013.01); *C07C 229/24* (2013.01); *C07C 229/26* (2013.01); *C07C 237/06* (2013.01); *C07C 275/16* (2013.01); *C07C 279/02* (2013.01); *C07C 323/58* (2013.01); *C07D 207/16* (2013.01)

(58) Field of Classification Search

CPC .. A61K 31/197; A61K 31/198; A61K 31/205; A61K 31/185; C07C 279/02; C07C 229/08; C07C 229/26; C07C 275/16

See application file for complete search history.

(56) References Cited

U.S. PATENT DOCUMENTS

| | | | |
|---|---|---|---|
| 1,916,983 | A | 7/1933 | McKee |
| 2,176,144 | A | 10/1939 | Moskowitz |
| 2,553,533 | A | 5/1951 | Komarik |
| 3,230,036 | A | 1/1966 | Kappelmann |
| 3,552,978 | A | 1/1971 | Inklaar |
| 3,886,040 | A | 5/1975 | Chibata |
| 3,956,513 | A | 5/1976 | Clarke |
| 3,997,659 | A | 12/1976 | Knohl |
| 4,146,611 | A | 3/1979 | Ondetti |

(Continued)

FOREIGN PATENT DOCUMENTS

| | | |
|---|---|---|
| CN | 1056225 | 11/1991 |
| CN | 1049824 | 3/2000 |

(Continued)

OTHER PUBLICATIONS

Horowitz, B.Z., "Bromism from Excessive Cola Consumption," Clinical Toxicology, 35(3):315-320, 1997.

(Continued)

*Primary Examiner* — Sarah Pihonak

(74) *Attorney, Agent, or Firm* — Pacer K. Udall; Booth Udall, PLC

(57) ABSTRACT

A solid supplement composition comprising at least one non-ester nitrate compound and at least one isolated amino acid compound, wherein the at least one isolated amino acid compound is creatine, wherein the at least one isolated amino acid compound is a separate compound than the at least one non-ester nitrate compound, and wherein the solid supplement composition comprises an amount of nitrate ion ($NO_3$—) that is at least 0.33125 mg.

30 Claims, No Drawings

(56) References Cited

U.S. PATENT DOCUMENTS 4,273,937 A 6/1981 Gum
4,291,015 A 9/1981 Keith
4,379,177 A 4/1983 McCoy
4,678,670 A 7/1987 Tomic
4,687,782 A 8/1987 Brantman
4,743,614 A 5/1988 Terano
4,749,402 A 6/1988 Garrett
4,853,237 A 8/1989 Prinkkila
4,871,550 A 10/1989 Millman
4,976,960 A 12/1990 Grossman
4,996,067 A 2/1991 Kobayashi
5,008,118 A 4/1991 Iwanami
5,026,071 A 6/1991 Miraglia, Jr.
5,026,721 A 6/1991 Dudrick
5,242,697 A 9/1993 Luca
5,321,030 A 6/1994 Kaddurah-Daouk
5,411,569 A 5/1995 Hjersted
5,485,827 A 1/1996 Zapol
5,500,436 A 3/1996 Karl
5,543,430 A 8/1996 Kaesemeyer
5,576,351 A 11/1996 Yoshimura
5,624,906 A 4/1997 Vermeer
5,631,031 A 5/1997 Meade
5,679,704 A 10/1997 Schonafinger
5,767,160 A 6/1998 Kaesemeyer
5,904,924 A 5/1999 Gaynor
5,965,596 A 10/1999 Harris
5,968,544 A 10/1999 Howard
6,063,432 A 5/2000 Maxwell
6,114,379 A 9/2000 Wheelwright
6,136,339 A 10/2000 Gardiner
6,159,485 A 12/2000 Yu
6,172,098 B1 1/2001 Harris
6,277,884 B1 8/2001 De Tejada
6,337,349 B2 1/2002 Scafetta
6,451,341 B1 9/2002 Slaga
6,562,869 B1 5/2003 Hamilton
6,608,109 B2 8/2003 Allen
6,784,209 B1 8/2004 Gardiner
7,025,996 B1 4/2006 Miladinov
7,040,313 B2 5/2006 Fine
7,235,237 B2 6/2007 Loscalzo
7,777,014 B2 8/2010 Cattaruzza
7,777,074 B2 8/2010 Kramer
7,799,782 B2 9/2010 Munson
7,825,084 B2 11/2010 Harris
8,034,836 B2 10/2011 Kramer
8,048,921 B2 11/2011 Kramer
8,178,572 B2 5/2012 Kramer
8,183,288 B2 5/2012 Kramer
8,303,995 B1 11/2012 Bryan
8,455,531 B2 6/2013 Kramer
8,466,187 B2 6/2013 Kramer
8,470,865 B2 6/2013 Harris
8,569,368 B2 10/2013 Kramer
8,569,369 B2 10/2013 Kramer
8,703,719 B1 4/2014 Abraham
8,852,660 B2 10/2014 Miljkovic
8,883,205 B2 11/2014 Roehr
8,952,045 B1 2/2015 Kramer
8,952,046 B1 2/2015 Kramer
8,957,100 B1 2/2015 Kramer
8,957,101 B1 2/2015 Kramer
8,993,610 B2 3/2015 Harris
9,180,140 B2 11/2015 Lundberg
RE45,947 E 3/2016 Harris
RE46,372 E 4/2017 Miller
10,426,750 B1 10/2019 Kramer
10,472,322 B1 11/2019 Kramer
10,555,921 B1 2/2020 Kramer
10,646,508 B1 5/2020 Kramer
10,736,916 B1 8/2020 Kramer
10,736,917 B1 8/2020 Kramer
11,154,499 B2 10/2021 Nikolaidis
11,166,979 B1 11/2021 Kramer
11,260,096 B2 3/2022 Kramer
11,865,139 B2 1/2024 Kramer
12,227,483 B1 2/2025 Kramer
12,240,819 B1 3/2025 Kramer
12,448,357 B1 10/2025 Kramer
12,473,261 B2 11/2025 Kramer
12,522,568 B2 1/2026 Kramer
12,540,119 B2 2/2026 Kramer
2001/0002269 A1 5/2001 Zhao
2001/0011074 A1 8/2001 Piccolo
2001/0020007 A1 9/2001 Wiss
2001/0031784 A1 10/2001 Petersen
2001/0048952 A1 12/2001 Siskind
2001/0055617 A1 12/2001 Mattern
2001/0056069 A1 12/2001 Klaus
2002/0006532 A1 1/2002 Robin
2002/0022060 A1 2/2002 Mathur
2002/0065323 A1 5/2002 Crooks
2002/0119933 A1 8/2002 Butler
2002/0136802 A1 9/2002 Mehansho
2002/0147156 A1 10/2002 Petit
2003/0012744 A1 1/2003 Pedersen
2003/0014238 A1 1/2003 Xun
2003/0060503 A1 3/2003 Hamilton
2003/0062043 A1 4/2003 Fine
2003/0091615 A1 5/2003 Craig
2003/0097401 A1 5/2003 Bauman
2003/0119888 A1 6/2003 Allen
2003/0139354 A1 7/2003 Buccholz
2004/0001817 A1 1/2004 Giampapa
2004/0006140 A1 1/2004 Kaesemeyer
2004/0033292 A1 2/2004 Portman
2004/0048870 A1 3/2004 Amir
2004/0057926 A1 3/2004 Ochoa
2004/0058011 A1 3/2004 Petersson
2004/0087518 A1 5/2004 Verlaan
2004/0097401 A1 5/2004 Datta
2004/0126366 A1 7/2004 Kaddurah-Daouk
2004/0151815 A1 8/2004 Jensen
2004/0176335 A1 9/2004 Childs
2004/0197430 A1 10/2004 Meyrowitz
2004/0224868 A1 11/2004 Meyerhoff
2004/0242682 A1 12/2004 Kaesemeyer
2005/0036949 A1 2/2005 Tucker
2005/0043274 A1 2/2005 Murad
2005/0043287 A1 2/2005 Allen
2005/0053673 A1 3/2005 Netke
2005/0171194 A1 8/2005 Yu
2005/0196474 A1 9/2005 Anno
2005/0256192 A1 11/2005 Gardiner
2005/0261257 A1 11/2005 Vermeer
2005/0266018 A1 12/2005 Boreyko
2005/0287210 A1 12/2005 Ron
2005/0288372 A1 12/2005 Ron
2005/0288373 A1 12/2005 Ron
2006/0014238 A1 1/2006 Gholap
2006/0018281 A1 1/2006 Sadot
2006/0029668 A1 2/2006 Ron
2006/0035007 A1 2/2006 Kawabe
2006/0063827 A1 3/2006 Yu
2006/0116328 A1 6/2006 Babizhayev
2006/0134227 A1 6/2006 Bortz
2006/0142382 A1 6/2006 Morimoto
2006/0182815 A1 8/2006 Gladwin
2006/0188607 A1 8/2006 Schramm
2006/0198899 A1 9/2006 Gardiner
2006/0239987 A1 10/2006 Foster
2006/0241181 A1 10/2006 Pola
2006/0275909 A1 12/2006 Spitzer
2007/0026109 A1 2/2007 Foulger
2007/0037880 A1 2/2007 Mailland
2007/0105817 A1 5/2007 Page
2007/0141174 A1 6/2007 Cornett
2007/0154569 A1 7/2007 Gladwin
2007/0166355 A1 7/2007 Brakstad
2008/0004218 A1 1/2008 Quay
2008/0026075 A1 1/2008 Kondo
2008/0038410 A1 2/2008 Giordano
2008/0064694 A1 3/2008 Heil

(56) References Cited

U.S. PATENT DOCUMENTS

| | | | |
|---|---|---|---|
| 2008/0138448 | A1 | 6/2008 | Heuer |
| 2008/0163793 | A1 | 7/2008 | Gernon |
| 2008/0194679 | A1 | 8/2008 | Ashmead |
| 2008/0214649 | A1 | 9/2008 | Yu |
| 2008/0233186 | A1 | 9/2008 | Romero |
| 2008/0233242 | A1 | 9/2008 | Zhang |
| 2008/0268095 | A1 | 10/2008 | Herzog |
| 2009/0018072 | A1 | 1/2009 | Scheele |
| 2009/0076110 | A1 | 3/2009 | Kramer |
| 2009/0137670 | A1 | 5/2009 | Kramer |
| 2009/0182044 | A1 | 7/2009 | Ashmed |
| 2009/0280199 | A1 | 11/2009 | Russell |
| 2009/0306208 | A1 | 12/2009 | Shimada |
| 2010/0004335 | A1 | 1/2010 | Kagami |
| 2010/0047344 | A1 | 2/2010 | Lundberg |
| 2010/0092441 | A1 | 4/2010 | Lundberg |
| 2010/0172890 | A1 | 7/2010 | Gilad |
| 2010/0297240 | A1 | 11/2010 | Bang-Andersen |
| 2011/0064712 | A1 | 3/2011 | Amato |
| 2011/0064720 | A1 | 3/2011 | Amato |
| 2011/0123654 | A1 | 5/2011 | Jaeger |
| 2012/0010211 | A1 | 1/2012 | Yuan |
| 2012/0220643 | A1 | 8/2012 | Kramer |
| 2013/0011377 | A1 | 1/2013 | Perrin |
| 2013/0071494 | A1 | 3/2013 | Bryan |
| 2013/0101704 | A1 | 4/2013 | Meehan |
| 2015/0246066 | A1 | 9/2015 | Nelson |
| 2017/0042935 | A1 | 2/2017 | Sakamoto |
| 2017/0303582 | A1 | 10/2017 | Lu |
| 2017/0306440 | A1 | 10/2017 | Hein |
| 2018/0055879 | A1 | 3/2018 | Novak |
| 2018/0133247 | A1 | 5/2018 | Green |
| 2020/0222449 | A1 | 7/2020 | Nikolaidis |
| 2020/0275685 | A1 | 9/2020 | Catanese |
| 2020/0405662 | A1 | 12/2020 | Kramer |
| 2021/0220422 | A1 | 7/2021 | Parker |
| 2021/0355191 | A1 | 11/2021 | Sherman |
| 2022/0143080 | A1 | 5/2022 | Kramer |
| 2023/0201115 | A1 | 6/2023 | Nikolaidis |
| 2025/0162996 | A1 | 5/2025 | Kramer |
| 2025/0163000 | A1 | 5/2025 | Kramer |

FOREIGN PATENT DOCUMENTS

| | | | | |
|---|---|---|---|---|
| CN | 1631539 | | 6/2005 | |
| CN | 20041009958 | | 6/2005 | |
| CN | 1781486 | | 6/2006 | |
| CN | 109480107 | | 3/2019 | |
| CN | 110680809 | | 1/2020 | |
| EP | 0031284 | | 7/1981 | |
| EP | 0454396 | | 10/1991 | |
| EP | 797992 | | 1/1997 | |
| EP | 1336602 | | 8/2003 | |
| EP | 1429829 | | 11/2013 | |
| EP | 2896302 | | 7/2015 | |
| GB | 1089084 | | 11/1967 | |
| GB | 2008578 | | 6/1979 | |
| GB | 2052976 | | 2/1981 | |
| GB | 2354441 | | 3/2001 | |
| HR | 20140504 | A2 | 12/2015 | |
| JP | 2010519335 | | 6/2010 | |
| JP | 2012529909 | | 11/2012 | |
| JP | 2014513527 | | 6/2014 | |
| JP | 2014122162 | | 7/2014 | |
| KR | 20110015141 | | 2/2011 | |
| WO | 9617604 | | 6/1996 | |
| WO | 1996017604 | | 6/1996 | |
| WO | 9843499 | | 10/1998 | |
| WO | 1999045797 | | 9/1999 | |
| WO | 9966921 | A1 | 12/1999 | |
| WO | 0040217 | | 7/2000 | |
| WO | WO-0074500 | A1 * | 12/2000 | ................ A61P 3/02 |
| WO | 0117525 | | 3/2001 | |
| WO | 20010126642 | | 4/2001 | |
| WO | 2001035953 | | 5/2001 | |
| WO | WO-0135953 | A2 * | 5/2001 | ................ A61P 9/08 |
| WO | 0195897 | | 12/2001 | |
| WO | 2002012882 | | 2/2002 | |
| WO | 03063789 | | 8/2003 | |
| WO | 2005062713 | | 7/2005 | |
| WO | 2005115175 | A1 | 12/2005 | |
| WO | 2006025286 | | 3/2006 | |
| WO | 2006124161 | | 11/2006 | |
| WO | 2007000985 | | 1/2007 | |
| WO | 2007066642 | | 6/2007 | |
| WO | 2007073398 | | 6/2007 | |
| WO | 2007093808 | | 8/2007 | |
| WO | 2008009615 | | 1/2008 | |
| WO | 2008028951 | | 3/2008 | |
| WO | 2008028951 | A1 | 3/2008 | |
| WO | 2008043855 | | 4/2008 | |
| WO | 2008105730 | | 9/2008 | |
| WO | 2008105731 | | 9/2008 | |
| WO | 2010147751 | | 12/2010 | |
| WO | 2018019663 | | 2/2018 | |
| WO | 2018071988 | | 4/2018 | |
| WO | 2020160509 | | 8/2020 | |
| WO | 2020214841 | | 10/2020 | |
| WO | 2021188163 | | 9/2021 | |
| WO | 2022104157 | | 5/2022 | |
| WO | 2022192743 | | 9/2022 | |

OTHER PUBLICATIONS http://www.beyondsupplements.com.au/index.php?route=product/, no date given. 5 pages.

http://www.bodybuilding.com/store/fuel-one/6th-gear.html, no date given. 4 pages.

http://www.curezone.org, no date given. 5 pages.

http://www.dymatize.com/store/workoutsupport/M-P-ACT-Energy, no date given. 4 pages.

http://www.ergo-log.com/plaatjes/xpand2x.gif, no date given.

https://nuts.com/cookingbaking/powders/beet.html, 2016.

https://www.thesynergycompany.com/organic-carrot-juice-powder, no date given.

Hu, "A Study on Elemental Irons and Iron Compounds for Food Fortification", 18th International Congress of Nutrition, pp. 1-9, Sep. 2005.

Hunter et al., "The Inhibition of Arginase by Amino Acids", Department of Pathological Chemistry, University of Toronto, Canada, Jul. 24, 1944. 20 pages.

Hunter, A., "Creatine and creatinine", Longmans, Green and Company Limited, 1928.

Hurrell et al. The Usefulness of Elemental Iron for Cereal Flour Fortification: A Sustain Task Force Report, Nutrition Reviews, Dec. 2002, pp. 391-406. (Year: 2002).

Huxtable et al., "Physiological actions of taurine", Physiological Reviews, 72(1):101-142, 1992.

Huynh, et al., "Amino acids, arginase and nitric oxide in vascular health", Clin. Experim. Pharmacol. 33(1-2): 1-8, Jan.-Feb. 2006.

Hyde, PJ et al., "The Reaction Between Aluminum Metal and Aqueous Solutions of the Nitrite Ion", Austalian Journal of Chemistry, vol. 33, No. 1, Jan. 1, 1980 (Jan. 1, 1980), p. 169, XP093223550, AU, ISSN:0004-9425, DOI: 10.1071/CH9800169.

IForce Nutrition product "Potassium Nitrate", 2006. 2 pages.

Ignarro et al., "Pharmacological evidence that endothelium-derived relaxing factor is nitric oxide: use of pyrogallol and superoxide dismutase to study endothelium-dependent and nitric oxide-elicited vascular smooth muscle relaxation.", The Journal of Pharmacology and Experimental Therapeutics, 1988., 244(1): 181-189.

Ignarro et al., "Pharmacology of Endothelium-derived Nitric Oxide and Nitrovasodilators", The Western Journal of Medicine, Jan. 1991, 154. 9 pages.

Ignarro, "After 130 years, the molecular mechanism of action of nitroglycerin is revealed," [online], Jun. 11, 2002 [retrieved on May 8, 2016]. Retrieved from the Internet: <http://www.pnas.Org/cgi/content/full/99/12/7816?ck=nck>). 2 pages.

Ilczyszyn et al. CAS: 145:83630 2006. 2 pages.

(56) References Cited

OTHER PUBLICATIONS

Ilczyszyn, et al., “13C chemical shift tensors of hydrogen bonded amino acids: relations between experimental and calculated results”, Chemical Physics, 323:231-242, 2006.
Imai, S., et al.,“Anti-arrhythmic effects of (--)-carnitine chloride and its acetyl analogue on canine late ventricular arrhythmia induced by ligation of the coronary artery as related to improvement of mitochondrial function” , Br. J. Pharmacol. 82:533-542, 1984.
Imaizumi, et al., “Effects of L-arginine on forearm vessels and responses to acetylcholine”, Hypertension, 20 (4):511-517, 1992.
Inchem “Safety information on Morpholine”, EHC 179, 1996, Retrieved Feb. 4, 2020. 77 pages. http://www.inchem.org/ documents/ehc/ehc/ehc179.htm.
Inchem (International Programme on Chemical Safety), “Information on Lead, Inorganic”, May 1994, 26 pages.
Ingested Nitrate and Nitrite, and Cyanobacterial Peptide Toxins, World Health Organization International Agency for Research on Cancer (2010) 24 pages.
International Organization for Standardization, “Meat and meat products—Determination of Nitrate content (Reference method)”, ISO 3091-1975, pp. 1-8, 1975.
Lonic Liquids ( URL: https://www.organic-chemistry.org/topics/ionic-liquids.shtm ), printed Apr. 2019 (Year: 2019). 4 pages.
Ishibashi et al. “Coronary hyperfusion augments myocardial oxygen consumption” Am J Physiol : Heart Circ. Physiol. 271(4): H1384-H1393,1996. https://doi.org/10.1152/ajpheart. 1996.271.4.H1384.
Ishii et al., “High glucose augments arginase activity and nitric oxide production in the renal cortex,” Metabolism 53(7):868-874 (2004).
J. Abrams, MD, Beneficial Actions of Nitrates in Cardiovascular Disease, The American Journal of Cardiology, vol. 77, pp. 31C-37C (May 30, 1996).
Jablecka et al., “The influence of two different doses of L-arginine oral supplementation on nitric oxide (NO) concentration and total antioxidant status (TAS) in atherosclerotic patients,” Med Sci Monit 10(1):CR29-32 (2004).
Jamalian et al., “Nutritional Value of Middle Eastern Foodstuffs”, Jamalian & Pellett: Nutritional Value of Middle Eastern Foodstuffs. IV, Dec. 1967. 5 pages.
Jones et al. “Nitric oxide synthase inhibition with L-NAME reduces maximal oxygen uptake but not gas exchange threshold during incremental cycle exercise in man” J Physiol 560.1:329-338, 2004.
Joy et al., “A multi-ingredient, preworkout supplement is apparently safe in healthy males and females,” Food & Research, 59:27470, 2015, 7 pages.
K. Tsuchiya, et al., Malfunction of Vascular Control in Lifestyle-Related Diseases: Formation of Systemic Hemoglobin-Nitric Oxide Complex (HbNO) From Dietary Nitrite, J. Pharmacol Sci, vol. 96, pp. 395-400 (2004).
Kanaya, et al., “Effects of L-arginine on lower limb vasodilator reserve and exercise capacity in patients with chronic heart failure”, Heart, 81:512-517, 1999.
Karlic, H and Lohninger, A. “Supplementation of L-carnitine in athletes: does it make sense?”, Nutrition. 20:709-715, 2004.
Kemmerer et al., “The essential amino acid content of several vegetables”, J. Nutr., 1949, 38(4): 527-33.
Kendrick et al., “The effect of 4 weeks B-alanine supplementation and isokinetic training on carnosine concentrations in type 1 and II human skeletal muscle fibres”, Eur J Appl Physiol (2009) 106:131-138, Feb. 12, 2009.
Kenechuwu et al., “Novel solidified reverse micellar solution-based mucoadhesive nano lipid gels encapsulating miconazole nitrate-loaded nanoparticles for improved treatment of oropharyngeal candidiasis”, J. Microencapsul, 2017, 34(6):592-609.
Kernohan et al., “An oral yohimbine/L-arginine combination (NMI 861) for the treatment of male erectile dysfunction: a pharmacokinetic, pharmacodynamic and interaction study with intravenous nitroglycerine in healthy male subjects”, British Journal of Clinical Pharmacology, © 2004 Blackwell Publishing Ltd. 9 pages.
Knot, “Nitrate Tolerance in Hypertension: New Insight Into a Century-Old Problem,” Circ Res 93:799-801 (2003).
Kolb, Louis et al., “Oral Nitrate Increases Microvascular Reactivity and the Number of Visible Perfused Microvessels in Healthy Volunteers.” Journal of Vascular Research, 2017, vol. 54, p. 209-216.
Kou et al. application No. 200410009958.3, 2005. 27 pages.
Kouzenkov V.S. et al., “Sodium potassium effect on development of nerological deficiency in experimental model of brain ischemia”, Moscow University Bulletin Ser. 16. Biology, (20140000), vol. 4, pp. 9-14, XP055831436.
Kramer et al., U. S. Patent Application Publication No. 2009/076110 A1 published Mar. 19, 2009. 12 pages.
Kumar et al., “Chemical Denitrificaiton of Water by Zero-Valent Magnesium Powder.” Journal of Hazardous Materials, vol. 135, No. 1-3, Jul. 31, 2006, pp. 112-121.
Kuo & Schroeder, “The emerging multifaceted roles of nitric oxide”, Annals of Surgery, 221(3)220-235, 1995.
Kurrek, MM, “Inhaled nitric oxide does not alter endotoxin-induced nitric oxide synthase activity during rat lung perfusion” J. Appl. Physiol. 79(4), 1088-1092, 1995.
Shi et al. “Vegetables: horticulture and processing” (Chapter 170), Handbook of Food Science, Technology, and Engineering, Hui, YH. (ed.) CRC Press, Boca Raton, FL., vol. 4, pp. 170-171 to 170-9, 2006.
Shinbo, T. et al., “Breathing nitric oxide plus hydrogen gas reduces ischemia-reperfusion injury and nitrotyrosine production in murine heart”, American Journal of Physiology Heart and Circulatory Physiology, 2013, vol. 305, pp. H542-H550.
Shiraki et al., “The hypotensive mechanisms of the new anti-anginal drugN-(2-Hydroxyethyl) Nicotinamide Nitrate (SG-75) in beagle dogs,” Japan. J. Pharmacol. vol. 31:921-929 (1981).
Simplicio et al. “Prodrus for Amines”, Molecules 2008, vol. 13, pp. 519-547.
Slart et al., “Nitrate Administration Increases Blood Flow in Dysfunctional but Viable MyocardiumLeading to Improved Assessment of Myocardial Viability: A Pet Study,” J. Nucl. Med. vol. 47: 1307-1311 (2006).
Smiechowska, M., “The content of nitrates V and III and Vitamin C in juices obtained from organic and conventional raw materials”, Polish J. Food Nutr. Sci. 12/53(2):57-61, 2003.
Smith et al., “Nitric oxide precursors and congenital heart surgery: A randomized controlled trial of oral citrulline,” J. Thorac Cardioasc Surg 132:52-65 (2006).
Source Naturals. L-ornithine. https://web.archive.org/web/20061110082314/http://www.sourcenaturals.com/products/GP1182, Nov. 10, 2006.
Sridhar et al., “L-Aspartic Acid Nitrate-L-Aspartic Acid,” Acta Cryst. E58:01372-01374 (2002) 1 page.
Srinivasan et al., “L-phenylalanine-nitric acid (2/1),” Acta Crystallographica E57:o916-o918, 2000.
Stahl, P.H., and Wermuth, C.G., “Handbook of Pharmaceutical Salts Properties, Selection and Use”, John Wiley & Sons, 2008.
Stedman’s Medical Dictionary for Health Professions and Nursing, 5th ed, Excerpt pages showing definitions for: “aerobic capacity”; “aerobic power”; “maximal oxygen consumption”; “maximal oxygen uptake”; “oxygen capacity”; “oxygen uptake”, “oxygen consumption”, 2005.
Stephany et al. “The intake of nitrate, nitrite and volatile N-nitrosoamines and the occurrence of volatile N-nitrosamines in human urine and veal calves”, IARC Scientific Publications, Jan. 1978, vol. 19, pp. 443-460 (Year: 1978).
Stephenson, Terence, “How children’s responses to drugs differ from adults,” Br. J. Clin. Pharmacol. 59(6): 670-673, Jun. 2005.
Stetson, C, “Characteristics of Adults vs. Children.” [retrieved on May 4, 2016]. Retrieved from the Internet <URL: ittp://www.ehow.com/info 8501147 characteristics-adults-vs-children.html>.
Stokes et al., “Long-Term Effectiveness of Extended-Release Nitrate for the Treatment of Systolic Hypertension”, Hypertension, 45:380-384, 2005.
Stout et al., “Effects of B-Alanine Supplementation on the onset of Neuromuscular Fatigue and Ventilatory Threshold in Women”, Amino Acids (2006), Springer-Verlag 2006. 6 pages.

(56) References Cited

OTHER PUBLICATIONS

Strecker, A., and Wislicenus, J., "Adolph Strecker's short text-book of organic chemistry", p. 423, D. Appleton, 1882.
Stryer, L., "Biochemistry", Third Edition, W.H. Freeman and Company, New York: 1988, pp. 15-24, 233-236, 261-268, 499-502 and 933-936.
Sugino et al., "L-ornithine supplementation attenuates physical fatigue in healthy volunteers by modulating lipid and amino acid metabolism," Nutrition Research, 2008, 28:738-743.
Sulcius, A., "Reactions of Metals in Nitric Acid: Writing Equations and Calculating Electromotive Force of Redox Reaction", (J. Chem. Educ. 2015;92:1971-1972). (Year: 2015) 6 pages.
Summary of Studies of B-Alanine and sports performance, "Studies of B-Alanine Supplementation on Exercise Capacity or Performance", Nov. 2011. 5 pages.
Sunderland et al. "VO2max and ventilatory threshold of trained cyclists are not affected by 28-day L-arginine supplementation" J Strength and Conditioning Research, 25(3):833-837, Mar. 2011.
Swensen et al. publication, Intl. J. of Sports Medicine, 1994, 15(7):430-4.
Symonds, B., "The influence of overweight and underweight on vitality", J. Med. Soc., New Jersey, V(4):159-167, 1908.
Takahashi et al., "Characterization of the influence of nitric oxide donors on intestinal absorption of macromolecules," International Journal of Pharmaceutics 286:89-97 (2004).
Tan et al. "Taurine protects against low-density lipoprotein-induced endothelial dysfunction by the DDAH/ADMA pathway," Vascular Pharmacology 46:338-345 (2007).
Tanaka, et al., "Effect of Nifedipine, Dilazep, Dinitrates and Propranolol on Blood Lactate Accumulation during Intensive Graded Exercise Testing in Healthy Young Subjects", Jpn Heart J, pp. 617-630, Sep. 1988.
Tang Chuan-Feng et al.: "Possibility of magnesium supplementation for supportive treatment in patients with COVID-19", European Journal of Pharmacology, Elsevier Science, NL, vol. 886, Sep. 12, 2020 (Sep. 12, 2020), XP086288713, ISSN: 0014-2999, DOI: 10.1016/J.EJPHAR.2020.173546.
Tannenbaum et al., "Inhibition of nitrosamine formation by ascorbic acid," Am. J. Clin. Nutr. 53: 2475-2505, 1991.
Tao, Guo-Hong et al., New Generation Ionic Liquids: Cations Derived From Amino Acids, The Royal Society of chemistry, ChemComm, Jun. 9, 2005, 3562-3564.
Taurine from Nutrabio, 2006. 3 pages.
Teragawa et al. (Heart, 86:212-216, 2001) Magnesium causes nitric oxide independent coronary artery vasodilation in humans.
Terzyan et al., "L-Arginine Nitrates," Journal of Molecular Structure 687:111-117 (2004).
Thandani, U. "Challenges with Nitrate Therapy and Nitrate Tolerance: Prevalence, Prevention, and Clinical Relevance" Am J Cardiovasc Drugs, 2014, vol. 14, pp. 287-301. (Year: 2014).
Thatcher, Gregory R. J., "Nitrates and NO release: contemporary aspects in biological and medicinal chemistry," Serial Review: Mechanisms and Novel Directions in the Biological Applications of Nitric Oxide Donors, Free Radical Biology & Medicine, vol. 37, No. 8, pp. 1122-1143 (2004).
The product APS Creatine Nitrate , for sale, 2014. 1 page.
The product Isoleucine nitrate power with a Brand name Hobid, for sale, 2014. 1 page.
The product L-glutamine nitrate power with a Brand name Hobid, for sale, 2014. 1 page.
The product L-Leucine nitrate power by Body Ripped, for sale, 2014. 1 page.
The product valine nitrate power with a Brand name Hobid, for sale, 2014. 1 page.
Thorpe, E., "A Dictionary of Applied Chemistry", J. Soc. Chem. Indust., 1924.
Todorov, V. et al., "Endogenous Nitric Oxide Attenuates Erythropoietin Gene Expression in Vivo", Pflugers Arch 2000; 439: 445-448.
Tong, WQ., "Salt screening and selection: new challenges and considerations in the modern pharmaceutical R&D program", Novartis, Pharmaceuticals Corporation Integrated Drug Product Development Process, 3-day course, University of Utah, Jul. 17-19, 2006.
Tricker, AR. et al., "Secondary Amine Precursors to Nitrosamines in Human Saliva, Gastric Juice, Blood, Urine, and Faeces", Carcinogenesis, 13, 563-568, 1992.
Tsuchiya, "Nitrite is an alternative source of No. In vivo", Am. J. Physil. Heart Circ., Physiol 288: H2163-H2170, 2004.
Tuomy, J.M., "Freeze drying of foods for the armed services" Technical report 70-43-FL, US Army Natick Laboratories, Feb. 1970.
Twin Lab Creatine Nitrate Fuel (product), 2004, URL: https://web.archive.org/web/20041211014326/http://www.twinlab.com:80/spn-product.cfm?Product_ID=1093&Subcategory_ID=MASS, Retrieved Dec. 22, 2017.
U.S. Department of Commerce, "The Atmosphere", National Oceanic and Atmospheric Administration , retrieved on Nov. 13, 2024, https://www.noaa.gov/jetstream/atmosphere.
U.S. Food & Drug Administration document with respect to 21 CFR §184.1878 for thiamine mononitrate (Year: 2018) 2 pages.
Bryan, Nathan S., Food, Nutrition and the Nitric Oxide Pathway, Biochemistry and Bioactivity, pp. 59-63, DESTech Publications, Inc., Lancaster PA, (2010).
BSN Volumaize Aretic Blast, on line, sale product, 2014. 1 page.
Burtscher. The Proonged Intake of L-Arginine-L-Aspartate Reduces Blood Lactate Accumulation and Oxygen Consumption During Submaximal Exercise, Journal of Sports Science and Medicine, vol. 4, pp. 314-322 (2005).
Calka, J., "The Role of Nitric Oxide in the Hypothalmic Control of LHRH and Oxytocin Release, Sexual Behavior and Aging of the LHRH and Oxytocin Neurons", Folia Histochem Cytobiol., 2006; 44(1):3-12.
Carbonyl diamine [online] retrieved on Aug. 18, 23 from: https://www.chembk.com/en/chem/Carbonyl%20diamine; 1 page. (Year: 2023).
Carpentier, A, et al., "Nitrate Supplementation, Exercise, and Kidney Function: Are There Detrimental Effects?", Med. Sci. Sports Exerc. 47(7):1519-1522, 2015.
CAS Registry No. 89695-59-0 https://chem.nlm.nih.gov/chemidplus/m/89695-59-0, 1984. 1 page.
Cavassa et al. W098/43499. International Publication Date: Oct. 8, 1998. 33 pages.
Cederqvist et al., "Direct Demonstration of NO Formation In Vivo From Organic Nitrites and Nitrates, and Correlation to Effects on Blood Pressure and to In Vitro Effects", Biochemical Pharmacology, vol. 47, No. 6, pp. 1047-1053, 1994.
Ceremuzynski L. et al., "Effect of Supplemental Oral L-Arginine on Exercise Capacity in Patients with Stable Angina Pectoris", The American Journal of Cardiology, vol. 80, pp. 331-333, 1997.
Cerretelli, P and Marconi, C., "L-carnitine supplementation in humans. The effects on physical performance.", Int. J. Sports Med, 11 (1990):1-14.
CFIndustries, "Material Safety Data Sheet for Urea Ammonium Nitrate Solution (UAN)," available at www.cfindustries.com/pdf/UANMSDS.pdf Oct. 25, 2006. 13 pages.
Chabot et al., "Characterization of the vasodilator properties of peroxynitrite on rat pulmonary artery: role of poly (adenosine 5' -diphosphoribose synthase," British Journal of Pharmacology 121: 485-490 (1997).
Chang et.al. Arginase Modulates Nitric Oxide Production in Activated Macrophages. Am. J. Physiol., 1998, H342-H348.
Chauhan et al., "Advancements in the Co-Formulation of Biologic Therapeutics", Journal of Controlled Release, 2020;327:397-405. (Year: 2020).
Chemical Abstracts (ACS), "Creatine nitrate. Inorganic Chemicals and Reactions", vol. 56, The Ohio State University, 1962.
Chemical Abstracts Service, "Chemical Abstracts", The American Chemical Society, Liquid Crystals, vol. 104, Jun. 2, 1986. 2 pages.
Chen Zhonglin, "Efficacy of Zero-valentZinc in Reducing Edema with Trace Nitrosodimethylamine," Journal of harbin Institute of technology, vol. 42, No. 12, pp. 1879-1882. Dec. 31, 2010.
Chick, TW, et al., "The effect of antihypertensive medications on exercise performance: a review", Med. Sci. Sports Exercise. 20(5):447-454, 1988.

(56) References Cited

OTHER PUBLICATIONS

Chong, "Relationship Between Circulating Levels of Nitrates and Steroid in Patients Admitted to Coronary Care Unit", a thesis submitted to fulfill the requirements of the Degree of Master of Science to the Chinese University of Hong Kong, 2002.
Chow, CK and Hong CB, "Dietary vitamin E and selenium and toxicity of nitrite and nitrate", Toxicology 180(2):195-207, 2002.
Clarkson, et al., "Oral L-arginine improves endothelium-dependent dilation in hypercholestolemic young adults", J. Clin. Invest. 97(8):1989-1994. 1996.
Colormaker, 2006. 1 page.
Cortas & Wakid. "Pharmacokinetic Aspects of Inorganic Nitrate Ingestion in Man", Pharmacol & Toxicol. 68:192-195, 1991.
Cosby et al., "Nitrite reduction to nitric oxide by deoxyhemoglobin vasodilates the human circulation", Nature Medicine, vol. 9, No. 12, Dec. 2003. 9 pages.
Cottrell et al. (J Physiol 595.15 (2017) pp. 5095-5102, Dietary interventions for fetal growth restriction—therapeutic potential of dietary nitrate supplementation in pregnancy (Year: 2017).
Cottrell, E. et al., "Dietary interventions for fetal growth restriction—therapeutic potential of dietary nitrate supplementation in pregnancy", J. Physiol. 595(15):5095-6102, 2017.
CPG Sec 565.100 FDA Jurisdiction Over Meat and Poultry Products, 2005. 3 pages.
Craig, Betaine in human nutrition, 1 Am J Clin Nutr, 80:539-549,2004.
Crawford et al., "Effect of nitrate on determinants of myocardial oxygen consumption during exercise", International Journal of Cardiology, 1, 307-314, 1982.
Crawford et al., "Hypoxia, Red Blood Cells, and Nitrite Regulate NO dependent Hypoxic Vasodilation", Blood 2006, 107:566-574.
Creatine from Wikipedia, 2017. 2 pages.
Creatine nitrate from PubChem, 2017. 1 page.
Cromwell et al., "The Biosynthesis and Metabolism of Betaines in Plants," 1953 Biochem J., 55: 189-192.
Curry, et al., "Phase 1 dose escalation trial of feverfew with standardized doses of parthenolide in patients with cancer", Invest. New Drugs, 22(3), 299-305, 2004.
Curry, M.D., Steven, "Methemoglobinemia", Ann Emerg Med, 11, 214-221, 1982.
Curtis, J., Dec. 6, 2017, "Nitrate-Free Bacon: Myth or Reality", https://firsthandfoods.com/author/jennifer/, pp. 1-2 Year: 2017).
D. Bendahan et al., "Citrulline/Malate Promotes Aerobic Energy Production in Human Exercising Muscle," Br. J. Sports Med. 36:282-89 (2002).
D. D. Rees, et al., Role of endothelium-derived nitric oxide in the regulation of blood pressure, Proc. Natl. Acad. Sci. USA, vol. 86, pp. 3375-3378 (May 1989).
Danov et al., "Mixed Solutions of Anionic and Zwitterionic Surfactant (Betaine): Surface Tension Isotherms, Adsoprtionand Relaxation Kinetics," Langmuir 20:5445-5453 (2004).
De Backer, et al., "Effects of dobutamine on the relationship between oxygen consumption and delivery in healthy volunteers: comparison with sodium nitroprusside", Clin Sci 90:105-111, 1996.
Declaration of Aram M. Petrosyan under 1.132, Nov. 7, 2013., submitted in US Reexam Nos. 90/011,869 and 90/011,869.
Declaration of Donald Monkhouse under 37 CFR 1.132, Jul. 26, 2017. 7 pages.
Declaration of James L. Bono under 37 CFR 1.132, Aug. 27, 2014. 13 pages.
Declaration of Jon Fukuto under 37 CFR 1.132, Jan. 6, 2020, submitted in U.S. Appl. No. 14/621,738.
Declaration of Jon Lundberg and Eddie Weitzberg under 37 CFR 1.132, Aug. 2016.
Declaration of Jon Lundberg and Eddie Weitzberg under 37 CFR 1.132, May 17, 2016.
Declaration of Mauro Di Pasquale under 37 CFR 1.132, undated, including Exhibits A and B. 15 pages.
Declaration of Rainer Böger under 37 CFR 1.132. Jul. 19, 2017.
Declaration of Richard Chamberlain under 37 CFR 1.132, Aug. 15, 2014, Filed in reexam, control Nos. 90/011,869 and 90/011,869, 4 pages.
Udintsev. Nitrates and physical performance. Siberian fiber. Sep. 8, 2018. [on-line] [ retrieved on Jun. 29, 2020] (Retrieved from the Internet: https://tfzp.rU/zdorovyj-obraz-zhizni/v/nitraty/ nitraty-i-fizicheskaya-rabotosposobnostO, p. 2, paragraph 2—p. 3, paragraph 1, p. 4, paragraph 1.
Umbrello, Michele et al: "The Key Role of Nitric Oxide in Hypoxia: Hypoxic Vasodilation and Energy Supply-Demand Matching", Antioxidans & Redox Signaling, vol. 19, No. 14, Nov. 10, 2013 (Nov. 10, 2013), pp. 1690-1710, XP055558805, US ISSN: 1523-0864, DOI: 10.1089/ars.2012.4979.
Unitypoint.org information pages: "Are statins a lifelong commitment? ", Retrieved from https://www.unitypoint.org/livewel l/article.aspx?. id=a9 9fee12-14fc-4367-b512-e140b35efbba, Apr. 30, 2020, 6 pages.
Unlabeled photos, marked as Ex. J, submitted with Jun. 16, 2020 applicant remarks | U.S. Pat. No. 10,894,025 file history. 8 pages.
Urakami, M. et al., "Relationship between Structure and Permeability of Tryptophan Derivatives Across Human Intestinal Epithelial (Caco-2) Cells.", Z. Naturforsch., (2003), vol. 58C, pp. 135-142, XP055127040.
US Department of Labor, OSHA health information re: hexavalent chromium, undated. 3 pages.
USDA and HHS Agencies Work Together to Examine the Jurisdiction of Certain Food Categories, USDA & FDA, 2005, 2 pages.
USDA Regulation 64 FR 72168, Food Ingredients and Sources of radiation Listed or Approved for Use in the Production of Meat and Poultry, 1999, 28 pages.
USPTO Trademark registration certificate: Betancourt Sports Nutrition: "Ripped Juice" TM, reg. No. 3,968,519, May 31, 2011.
Usselman, M. et al., "Restaging Liebig: a study in the replication of experiments", Annals of Science, 62:1-55, 2005.
Valenti S. et al., "Biphasic Effect of Nitric Oxide on Testosterone and Cyclic GMP Production by Purified Rat Leydig Cells Cultured in Vitro", Int J Androl, 1999; 22:336-341.
Van Maanen, JM. et al., "Consumption of Drinking Water with High Nitrate Levels Causes Hypertrophy of the Thyroid", Toxicol Lett., Jun. 1994, 72(1-3): 365-74.
Van Maanen, JM. et al., "Formation of nitrosamines during consumption of nitrate- and amine-rich foods, and the influence of the use of mouthwashes", (Abstract) Cancer Detect Prev., 1998; 22(3):204-12. doi: 10.1046/j.1525-1500.1998.00a26.x.
Van Maanen, JM. et al., "Nitrate contamination of drinking water: relationship with HPRT variant frequency in lymphocyte DNA and urinary excretion of N-nitrosamines", Environ Health Perspect., May 1996; 104(5):522-8. doi: 10.1289/ehp.96104522.
Vandenberghe et al. publicaiton, J. Appl physiol, 1997, 83:2055-2063.
Vermeer, ITM., et al., "Volatile N-nitrosamine formation after intake of nitrate at the ADI level in combination with an amine-rich diet", Environmental Health Perspectives 106(8):459-463, 1998.
Vilskersts. R. et al. Magnesium nitrate attenuates blood pressure rise in SHR rats. Magnes Res. Jan.-Mar. 2014; 27(1):16-24. doi:10.1684/mrh.2014.0358. PMID: 24827813.
Von Liebig, Justus, "Über die Bestandtheile der Flüssigkeiten des Fleisches" Annalen der Chemieund Pharmacie. 62:293-298, 1847.
Vytech advertisement for "Nitrobol Extreme" Joe Weider's Muscle & Fitness, Sep. 2005. 2 pages.
Walker et al., Food additive and Contaminants, 1990, 7(6):717-768.
Walker, et al., "Endothelium-dependent vasodilation is independent of the plasma L-arginine/ADMA ratio in men with stable angina: Lack of effect of oral L-arginine on endothelial function, oxidative stress and exercise performance", J Am Coll Cardiol, 38(2):499-505, 2001.
Watt et al., "The Chemist, A Monthly Journal of Chemical & Physical Science", vol. 1, London; Samuel Highley, 32 Fleet Street, 1854. 5 pages.
Watts, "A Dictionary of Chemistry and the Allied Branches of Other Sciences", Library of the University of California, Aug. 1808. 5 pages.
Webb, AJ, et al., "Acute blood pressure lowering, vasoprotective and anti-platelet properties of dietary nitrate via bioconversion to

(56) References Cited

OTHER PUBLICATIONS nitrite", Hypertension. 51(3):784-790, Mar. 2008., DOI:10.1161/HYPERTENSIONAHA.107.103523.
Weissman BA. et al., "Paracrine Modulation of Androgen Synthesis in Rat Leydig Cells by Nitric Oxide", J Androl., May-Jun. 2005; 26(3):369-78.
Weitzberg et al., "Dietary Nitrate—A Slow Train Coming", J Physiol 589.22 (2011) pp. 5333-5533, 2011 The Authors. Journal compilation, 2011 The Physiological Society.
Westerhoff P. et al., "Nitrate removal in zero-valent iron packed columns", Water Research, Elsevier, Amsterdam, NL, vol. 37, No. 8, Apr. 1, 2003 (Apr. 1, 2003), pp. 1818-1830, XP004419942, ISSN: 0043-1354, DOI:10.1016/S0043-1354(02)00539-0.
White, Handler and Smith, Principles of Biochemistry, Fifth Edition, McGrawy-Hill, New York:1973, pp. 89-95.
Wieshammer et al., "Lack of effect of nitrates on exercise tolerance in patients with mild to moderate heart failure caused by coronary disease already treated with captopril", Br Heart J, 70:17-21, 1993.
Wilburne, M., and Uhley, M., "Effect of Procaine on the Heart," JAMA. 138(6):449, 1948.
Wilson et al., "Beta-Alanine-Bad Ass Supplement", Iron Man Magazine, Oct. 13, 2010. 14 pages.
Winter et al., "N-Nitrosamine Generation From Ingested Nitrate Via Nitric Oxide in Subjects With and Without Gastroesophageal Reflux," Gastroenterology, 2007, 133:164-174.
Wolinsky, et al., "Nutritional Applications in Exercise and Sport", Chapter 14, CRC Press, 1st ed, 2000.
Wu Chun et al., "Study on the Inhibition of Nitrosamine Synthesis by Quercetin-Zinc(II) Complexes in Vitro and In Vitro," Food Science, vol. 28, No. 9, pp. 35-38. Dec. 31, 2007.
Wwheatley et al., "Arginine deprivation and tumour cell death: Arginase and its inhibition," Molecular and Cellular Biochemistry, 244:177-185, 2003.
Wyngaarden, JB. et al., "The Effects of Iodine, Perchlorate, Thiocyn-ate, and Nitrate Administration Upon the Iodide Concentrating Mechanism of the Rat Thyroid", Endocrinology, May 1953, 52(5):568-74.
Ximenes et al. "Polarographic determination of nitrate in vegetables" Talanta, 2000, vol. 51, pp. 49-56. (Year: 2000).
Xu et al., "Composite medical preparation for promoting hair growth," CAS: 143:103285 (2005). 1 page.
Yailian, A-L., "Production and stability study of a hospital parenteral nutrition solution for neonates", J. Pharmaceutical Analysis, 9(2019):83-99, 2019.
Yoshii, et al., "Effect of mixed meal and leucine intake on plasma amino acid concentrations in young men" Nutrients, 10(10):1543, 2018.
Yu, B. et al., "Inhaled Nitric Oxide", British Journal of Pharmacology, Dec. 31, 2019, pp. 246-255, XP093223242, DOI: 10.1111/bph.v176.2/issuetoc.
Yu, Qin, et al., "Portable Nitric Oxide (NO) Generator Based on Electrochemical Reduction of Nitrite for Potential Applications in Inhaled NO Therapy and Cardiopulmonary Bypass Surgery" Mol Pharm, vol. 14, No. 11, Nov. 6, 2017, pp. 3762-3771, XP055963565.
Zhang et al. "Role of Taurine Supplementation to Prevent Exercise-Induced Oxidative Stress inhealthy Young Men" Amino Acids, 2004, 26:203-207.
Zhang X, et al. Effects of Magnesium Supplementation on Blood Pressure: A Meta-Analysis of Randomized Double-Blind Placebo-Controlled Trials. Hypertension. Aug. 2016;68(2):324-33. doi: 10.1161/HYPERTENSIONAHA.116.07664. Epub Jul. 11, 2016. PMID: 27402922.
Zhang Z. et al., "Reductive denitrification kinetics of nitrite by zero-valent iron", Desalination, Elsevier, Amsterdam, NL, vol. 257, No. 1-3, Jul. 1, 2010 (Jul. 1, 2010), pp. 158-162, XP027020374, ISSN: 0011-9164.
Zhang, et al., "Nitrite Reductase Reduces Nitrite Content of Pickles and Mitigates Intoxication in Nitrite-intoxicated Mice", Scientific Reports, Nature, 5:14907, 2015. doi:10.1038/srep14907.
Zhu et al., "Expression of Human Arginine Decarboxylase, the Biosynthetic Enzyme for Agmatine", NIH Public Access, Biochim Biophys Acta. Jan. 22, 2004; 1670(2): 156-164.
Ziegenfuss et al., "Effect of a Supplement Containing Primarily Beta Alanine, Arginine, Creatine Malate, and Glycerol Monostear-ate on Exercise-Induced Changes in Lean Mass of the Arms", Journal of the International Society of Sports Nutrition 2008, 5(Suppl 1):P16 doi:10.1186/1550-2783-5-S1-P16. 2 pages.
Ashenhurst ([online] retrieved on Aug. 18, 23 from: https://www.masterorganicchemistry.com/2018/02/28/ amides-properties-synthesis-and-nomenclature/ 3 pages) (Year: 2023).
Ashmore T. et al., "Suppression of Erythropoiesis by Dietary Nitrate", Mar. 2015, 29(3): 1102-12.
Astill, B. D. et al., "Phenolic Antioxidants amd the Inhibition of Hepatotoxicity from N-Dimethylnitrosamine Formed in Situ in the Rat Stomach" Food and Cosmetics Toxicology, Pergamon Press, Oxfrod, Grat Britain, vol. 15, No. 3, Jan. 1, 1977, pp. 167-171.
Atanasova, Plant Siol Environ, 2008, 54(2):66-71.
ATSDR—"Public health statement for nitrate and nitrite", https://www.atsdr.cdc.gov/phs/phs.asp?id=1448&tid=258, 2017.
ATSDR Case Studies in Environmental Medicine Nitrate/Nitrite Toxicity published by the U.S. Department of Health and Human Services on Dec. 5, 2013. ATSDR Case Studies in Environmental Medicine Nitrate/Nitrite Toxicity. 135 pages.
ATSDR public health statement: Perchlorates, Sep. 2008, 10 pages.
ATSDR, "Frequently asked questions: Calcium hypochlorite and Sodium hypochlorite", Apr. 2002, 2 pages.
Avraham et al., "Tyrosine improves appetite cognition and exercise tolerance in activity anorexia," Medicine & Science in Sports & Exercise, 33(12): 2104-2110, 2001.
B. C. Challis, Nutrition and nitrosamine formation, Proceeds of the Nutrition Society, vol. 44, pp. 95-100 (1985).
B. Pejin et al., Heavy metal content of a medicinal moss tea for hypertension, Natural Product Research, Taylor & Francis, 2012 vol. 26, No. 23, 2239-2242.
B. Pejin et al., Mineral Content of a Moss Tea for Hypertention, Italian Journal of Food Science , Italy Codon Publications, 2013 vol. 25, 235-237.
B. Spiegelhalder, et al., Influence of Dietary Nitrate on Nitrate Content of Human Saliva: Possible Relevance of N-Nitroso Compounds, Fd. Cosmet. Toxicol., vol. 14, pp. 545-548 (1976).
B. Sridhar, et al, "Bis (beta-alanine) Hydrogen Nitrate", Acta Crystallographica Section, 2001, pp. 1004-1006 vol. 57.
Bahadur et al., "Crystal and molecular stucture of DL-aspartic acid nitrate monohydrate," Z. Kristallogr. 210: 276-278, 1995.
Bailey et al. "Dietary nitrate supplementation reduces the 02 cost of low-intensity exercise and enhances tolerance to ligh-intensity exercise in humans", J. Appl. Physiol., 2009, vol. 107, pp. 1144-1155. (Year 2009).
Baran, "Crystal structure, phase transitions and vibrational spectra of bis(betaine) nitrate," Journal of Molecular Structure, 372:131-144, 1995.
Barclay & Stainsby. "The role of blood flow in limiting maximal metabolic rate in muscle" Med Sci Sports 7(2):116-119, 1975.
Barr, S., "Effects of dehydration in exercise performance", Can. J. Appl. Physiol.24(2):164-172, 1999.
Barrett, KE., "Carbohydrate, protein and water soluble vitamin assimilation" chapter 15, Gastrointestinal Physiology, McGraw-Hill, New York, NY, 2006.
Barron JT and Parillo JE, "Production of lactic acid and energy metabolism in vascular smooth muscle: effect of dichloroacetate." Am J Physiol. Feb. 1995;268(2 Pt 2):H713-9.
Basheva et al., "Role of Betaine as Foam Booster in the Presence of Silicone Oil Drops," Langmuir 16:1000-1013 (2000).
Bauer et al., "Vascular and Hemodynamic Differences Between Organic Nitrates and Nitrites," Journal of Pharmacology and Experimental Therapeutics 280:326-331 (1997).
Bauer JA, et al, "Photochemical Generation of Nitric Oxide from Nitro-containing Compounds: Possible Relation to Vascular Photorelaxation Phenomena", Life Science, 1994, 54, 1PL 1-4.
BeetV02Max—max Nitric Oxide Booster, Amazon.com, 2006. 1 page.

(56) References Cited

OTHER PUBLICATIONS

Beghetti et al. "Nitric oxide precursors and congenital cardiac surgery: A randomized controlled trial of oral citrulline. Definition of pulmonary hypertension in Fontan circulation?" J Thorac Cardioasc Surg 132(6): 1501-1502 (2006).
Belitz, H.D., & Grosch, W., "Food Chemistry", 2nd ed., Springer Berlin Heidelberg. 1999. Excerpts: pp. 8-15; pp. 548-549; & p. 467.
Benbrook, "Elevating antioxidant levels in food through organic farming and food processing", Jan. 2005.
Benjamin, Nigel, Nitrates in the Human Diet—good or bad?, Ann. Zootech. vol. 49, pp. 207-216 (2000).
Berge et al., "Pharmaceutical Salts," Journal of Pharmaceutical Sciences 66(1):1-18 (1977).
Betancourt product: Betancourt Ripped Juice EX2, 2006. 3 pages.
Beverly International advertisement, Joe Weider's Muscle & Fitness, Dec. 1987. 5 pages.
Bhatia A.L., Jain Manish, "Amaranthus paniculatus (Linn.) improves learning after radiation stress", Journal of Ethnopharmacology, Elsevier Ireland Ltd, IE, IE , (Mar. 1, 2003), vol. 85, No. 1, doi:10.1016/S0378-8741(02)00337-9, ISSN 0378-8741, pp. 73-79, XP093036506.
Bighley, et al. "Salt forms of Drugs and Absorption", in Encyclopedia of Pharmaceutical Technology, Swarbrick and Boylan, eds. Marcel Dekker Inc., New York, vol. 13, 1996.
Bjorne et al., "Nitrite in Saliva Increases Gastric and Mucosal Blood Flow and Mucus Thickness", J. Clin. Invest. 113:106-114, Jan. 2004.
Bjorne, "The Nitrite Ion: Its Role in Vasoregulation and Host Defenses", from the Department of Physiology and Pharmacology Section of Anesthesiology and Intensive Care Medicine, Karolinska Instititutet, Stockholm, Sweden, 2005.
Blodgett et al. "Incidence of Hematologic Disease in Patients with Carpal Tunnel Syndrome" JAMA, 1962, 182(7), pp. 814-815.
Bloomer et al., "Comparison of pre-workout nitric oxide stimulating dietary supplements on skeletal muscle oxygen saturation, blood nitrate/nitrite, lipid peroxidation, and upper body exercise performance in resistance trained men", Journal of the International Society of Sports Nutrition 2010, 7:16, http://www.jissn.com/content/7/1 /16. 15 pages.
Bloomer et al., "Glycine propionyl-L-carnitine increases plasma nitrate/nitrite in resistance trained men," Journal of the International Society of Sports Nutrition 4(22):1 1-6 (2007).
Bloxam, "Creatinine", Chemistry Nonorganic and Organic with Experiments, 1895.
Body S. C. et al., "Nitric Oxide: Delivery, Measurement, and Clinical Application", Journal of Cardiothoracic and Vascular Anesthesia, Elsevier, Amsterdam, NL, vol. 9, No. 6, Jan. 1, 1995, pp. 748-763, XP009009779, ISSN: 1053-0770, DOI: 10.1016/S1053-0770(05)80242-3.
Boger, "The Pharmacodynamics of L-Arginine," J. Nutr. 137:1650S-1655S (2007).
Boger, et al., "Dietary L-arginine and x-tocopherol reduce vascular oxidative stress and preserve endothelial function in hypercholesterolemic rabbits via different mechanisms", Atherosclerosis. 141(1) 31-43, 1998.
Boguslavskiy. Effect of nitric oxide on the efficiency of oxygen usage by a working skeletal muscle under fatigue, Fiziol. Zhum., vol. 51, No. 1, pp. 33-42 (2005) & Certified Translation.
Borison et al., "Brain 2-phenylethylamine as a major mediator for the central actions of amphetamine and methylphenidate," Life Sci. 17: 1331-1344, Nov. 1975.
Bover-Cid et al., "Biogeneic Amine Accumulation in Ripened Sausages Affected by the Addition of Sodium Sulphite", Meat Science 59 (2001) 391-396, Mar. 20, 2001.
Brock W.H., "Justus von Liebig: the chemical gatekeeper", Cambridge University Press, 1997.
Brooke, John Hedley. "Thinking about matter: studies in the history of chemical philosophy.", 1995.
Brunton, "Therapeutics of the Circulation", 2nd ed. Paul B. Hoeber, 1914.
Bryan, et al., "Bound NO in human red blood cells: fact or artifact?", Nitric Oxide, 10:221-228, 2004.
L. Brunton, An Address on Blood Pressure in Man: Its estimation and indications for treatment, The British Medical Journal, pp. 64-67 (Jul. 10, 1909).
L. Brunton, et al., An Address on Longevity and the Means of Attaining It, The Lancet, vol. 168, Issue 4342, pp. 1330-1335 (Nov. 17, 1906).
L. Noah et al., Starting from Scratch?: Reinventing the Food Additive Approval process, Boston Univ. L. Rev. vol. 78:329, pp. 329-443 1998.
La Brada Nutrition—Amino Thrust advertisement and posts on bodybuilding website, posted by Coach Chuck D. http://forum.bodybuilding.com/showthread.php?t=166071121 retrieved Aug. 23, 2016. 3 pages.
La Brada Nutrition—Amino Thrust advertisement from 2014, retrieved Aug. 23, 2016 from web archive: https://web.archive.org/web/20141110003235/web/http://www.labrada.com/store/amino_thrust.html 3 pages.
Lakhmir Singh ([online] retrieved on Dec. 18, 2024 from: https://www.google.com/books/edition/Lakhmir_Singh_s_Science_for_Class_8/ z2wtDAAAQBAJ?hl=en&gbpv=0; 2016; p. 70) (Year: 2016).
Large Wendy, "Circuit training combines aerobic and anaerobic workouts into one," News Journal (Mansfield Ohio), Sep. 5, 2004. 3 pages.
Larsen et al., "Effects of Dietary Nitrate on Blood Pressure in Healthy Volunteers," New England Journal of Medicine, 2006, 355:2792-2793.
Larsen et al., "Effects of Dietary Nitrate on Oxygen Cost During Exercise," Acta Physiol. 191: 59-66, 2007.
Larsson, S., et al., "Processed meat consumption, dietary nitrosamines and stomach cancer risk in a cohort of Swedish women", Int. J. Cancer. 119:915-919, 2006.
Larsson, S., et al., "Processed meat consumption and stomach cancer risk: a meta-analysis", J Nat. Cancer Institute, 98(15):1078-87, 2006.
Lauer, et al. "Plasma nitrite rather than nitrate reflects regional endothelial nitric oxide synthase activity but lacks intrinsic vasodilator action", PNAS, 98(22):12814-12819, 2001.
Laycock et al., "Role of Nitric Oxide in the Control of Renal Oxygen Consumption In the Regulation of Chemical Work in the Kidney", Circ. Res., 82:1263-1271, 1998.
Levere, T.H., "Affinity and matter: elements of chemical philosophy, 1800-1865", 1971.
Lewis et al. publication, Pharmacol. Biochem Behav, 2007, 88(1): 114-21.
Lijinsky, W. et al., "Nitrosation of Tertiary Amines and Some Biologic Implications", J. Natl. Cancer Inst., 49, 1239-1249, 1972.
Ilczyszyn et al. 13C chemical shift tensors of hydrogen bonded amino acids: Relations between experimental and calculated results. Chemical Physics 323 (2006) 231-242.
Lugasi, et al., "The role of antioxidant phytonutrients in the prevention of diseases", Acta Biologica Szegediensis, 47(1-4):119-125, 2003.
Luigi et al., "Acute amino acids supplementation enhances pituitary responsiveness in athletes", Med. Sci Sports Exerc, 1999, 31(12): 1748-54.
Lundberg et al., "Cardioprotective effects of vegetables: Is nitrate the answer?", Science Direct, Jan. 2006. 4 pages.
Lundberg et al., "NO generation from nitrite and its role in vascular control", Arterioscler. Thromb. Vasc. Biol., 25:915-922 (2005).
Lundberg et al., "The nitrate-nitrite-nitric oxide pathway in physiology and therapeutics", Nat Rev Drug Discov., 7(2):156-167, 2008.
Lundberg, "Inorganic Nitrate is a Possible Source for Systemic Generation of Nitric Oxide," Free Radical Biology & Medicine, vol. 37, No. 3, pp. 395-400, 2004.
Luscher, "Endogenous and exogenous nitrates and their role in myocardial ischaemia," Br. J. Clin. Pharmacol. 34:29S-35S (1992).
Maag et al."Nitrogenous Compounds in Sugarbeet Juices," Journal of the American Society of Sugar Beet Technologists 17(2):154-164 (1972).

(56) References Cited

OTHER PUBLICATIONS

MaCallister, RJ, "Arginine and Nitrate Tolerance", Br. J. Pharmacol. 130:209-210, 2000.
MacIntyre, JG, "The effect of oral arginine hydrochloride on growth hormone levels, body composition, performance and biochemical parameters in male recreational runners", University of British Columbia, MS Thesis, 1986.
Magnesium, Britannica Online Encyclopedia [online] retrieved on May 30, 24 from: https://www.britannica.com/print/article/356899; 3 pages.) (Year: 2024).
Manach, et al., "Polyphenols: food sources and bioavailability", Am. J. Clin. Nutr. 79:727-747, 2004.
Material Safety Data Sheet—beta-alanine. 5 pages. Print date Aug. 26, 2009.
Material Safety Data Sheet—Taurine, 5 pages. Print date Aug. 28, 2009.
Material Safety Data Sheet-L-Arginine. 5 pages. Print date Aug. 26, 2009.
Material Safety Data Sheet-L-Glutamine. 2008. 6 pages.
Material Safety Data Sheet-L-Leucine MSDS. 6 pages. Created 2005.
Material Safety Data Sheet-L-Norvaline. 2 pages. Date unknown.
Material Safety Data Sheet—agmatine sulfate salt, 2008. 3 pages.
Material Safety Datasheet: Piperidine. Feb. 4, 2020 6 pages.
Mauro di Pasquale website for FAQ [retrieved from web.archive.org for Aug. 9, 2016] using the link in paragraph 6 of his undated Declaration: http://www.mauromd.com/faqs.php, 42 pages.
Maynard et al."High Levels of Dietary Carnosine are Associated With Increased Concentrations of Carnosine and Histidine in Rat Soleus Muscle," J. Nutr. 131:287-290 (2001).
McDougall, J., "Plant foods have a complete amino acid composition", Circulation, 105(25), e197-e197, 2002.
McKnight et al., "Review article: Dietary nitrate in man: friend or foe?", British Journal of Nutrition, 81:349-358, 1999.
Merriam-Webster definition of supplement https://www.merriam-webster.com/dictionary/ supplementlaccessed Jun. 20, 2019] (Year: 2019) 13 pages.
Merriam-Webster definition of "dietary supplement" https://www.merriam-webster.com/dictionary/dietary%20supplement [accessed Jun. 20, 2019] (Year: 2019) 10 pages.
Millar et al., "Xanthine Oxidoreductase Catalyses the Reduction of Nitrates and Nitrite to Nitric Oxide Under Hypoxic Conditions", FEBS Letters 427, 225-228, 1998.
Miller, Elements of Chemistry—Theoretical and Practical, Longsmans, Green, Reader and Dyer, 1869, pp. 757-770.
Miller, TJ., "The kinetics and mechanism of the hydrolysis of creatinine in urine", Analytical Letters, 24(10):1779-1784, 1991.
Ming et al., "Thrombin Stimulates Human Endothelial Arginase Enzymatic Activity via RhoA/ROCK Pathway," Simulation 110:3708-3714 (2004).
Mirvish SS., "Role of N-Nitroso Compounds (NOC) and N-Nitrosation in Etiology of Gastric, Esophageal, Nasopharyngeal, and Bladder Cancer and Contribution to Cancer of Known Exposures to NOC", Cancer Lett., 1995, 93, 17-48.
Mirvish, S.S., "Blocking the formation of N-nitroso compounds with ascorbic acid in vitro and in vivo," Annals of New York Academy of Sciences. 1975; pp. 175-180) (Year: 1975).
Mirvish, SS., "Formation of N-Nitroso Compounds: Chemistry, Kinetics, and in Vivo Occurrence", Toxicol. Appl. Pharmacol., 31, 325-351, 1975.
Modine et al., "Nitrite-derived Nitric Oxide: a Possible Mediator of Acidic-Metabolic Vasodilation", Acta Physlol Scand, 171, 9-16, 2001.
Moncada et al., "The L-Arginine: Nitric Oxide Pathway", Journal of Cardiovascular Pharmacology, 17(Suppl. 3):S1-S9, Raven Press, New York, 1991.
Montenegro et al., "Profound differences between humans and rodents in the ability to concentrate salivary nitrate: Implications for translational research," Redox Biology 10:206-210, 2016.
Mostad et al."Crystal and molecular structure of DL-methionine nitrate," CAS 104:197543 (1986). 1 page.
Mostad, A., "Crystal and molecular structure of DL-methionine nitrate," Zeitschrift fur Kristallographie, 172: 175-182, 1985.
MrSupplement.com product dietary supplement Creatine Nitrate, 2006. 2 pages.
Mukohopadhyay, S. et al., "Evaluation of Possible Goitrogenic and Anti-Thyroidal Effect of Nitrate, a Potential Environmental Pollutant", Indian J Physiol Pharmacol, Jul.-Sep. 2005; 49(3):284-8.
Muramoto, J., "Comparison of Nitrate Content in Leafy Vegetables from Organic and Conventional Farms in California" Center for Agroecology and Sustainable Food Systems University of California, Santa Cruz, 1999. 66 pages.
Muscle & Fitness magazine, Dec. 1987.
Muscle & Fitness magazine, May 2006.
Muscle & Fitness magazine, Sep. 2005.
Nabrzyski, M., and Gajewska, R., "The content of nitrates and nitrites in fruits, vegetables and other foodstuffs", (Abstract in English), Rocz Panstw Zaki Hig, 45(3):167-80, 1994, 1 page.
Naidu, K., "Vitamin C in human health and disease is still a mystery? An overview", Nutr. J. 2(7):1-10, 2003.
National Library of Medicine, MeSH descriptor data for "Drug Carriers", 2020. 1 page.
Nature's Best advertisement for "Perfect L-Glutamine" Joe Weider's Muscle & Fitness, Sep. 2005. 2 pages.
NCBI bookshelf, "Continuing education activity re: Technetium-99m", printed Dec. 18, 2025. 8 pages.
Nesacaine label showing properties of chloroprocaine. Nov. 2018. 14 pages.
NIH—Facts bout the DASH diet. 2001.
NIH, "The Seventh Report of the Joint National Committee on Prevention, Detection, Evaluation and Treatment of High Blood Pressure", 2004.
Niu et al., "Vasorelaxant effect of taurine is diminished by tetraethylammonium in rat isolated arteries," European Journal of Pharmacology 580:169-174 (2008).
Novitskii, W., et al., "Mechanisms of hemolytic anemia during experimental methemoglobinemias" (Abstract), Bull. Exp. Biol Med. 142(5):565-569, 2006.
NutraBioBCAA2500, 2006. 1 page.
Oka et al."A pilot study of L-arginine supplementation on functional capacity in peripheral arterial disease," Vascular Medicine 10:265-274 (2005).
Oldreive, C, Rice-Evans, C, "The Mechanisms for Nitration and Nitrotyrosine Formation in vitro and in vivo: Impact of Diet", Free Rad. Res., vol. 35, pp. 215-231, 2001.
Optimum Nutrition advertisement for "Adenergy Stack" Joe Weider's Muscle & Fitness, Sep. 2005. 2 pages.
Owlya, et al. "Cardiovascular and sympathetic effects of nitric oxide inhibition at rest and during static exercise in humans" Circulation 96:3897-3903, 1997. https://doi.org/10.1161/01.CIR.96.11.3897.
Pace, S., et al., "Pharmacokinetics of propionyl-L-carnitine in humans: evidence for saturable tubular reabsorption", Br. J. Clin. Pharmacol. 50:441-448, 2000.
Panesar N., and Chan, K., "Decreased steroid hormone synthesis from inorganic nitrite and nitrate: studies in vitro and in vivo" Toxicol. and Applied Pharmacol. 169:222-230, 2000.
Panesar NS. et al., "Decreased Steroid Hormone Synthesis from Inorganic Nitrate and Nitrate: Studies in Vitro and In Vivo", Toxicol Appl Pharmacol., Dec. 15, 2000, 169(3):222-30.
Pannala, et al., "The effect of dietary nitrate on salivary plasma and urinary nitrate metabolism in humans", Free Radical Biology & Medicine, 34(5):576-584, 2003. doi:10.1016/S0891-5849(02)01353-9.
Parent et al., "Nitroglycerin reduces myocardial oxygen consumption during exercise despite vascular tolerance", Am J Physiol Heart Circ Physlol 290: H1226-H1234, 2005.
Pariser et al., "Oxiconazole nitrate lotion, 1 percent: an effective treatment for tinea pedis", Cutis, 1994, 54(1): 43-44.
Parker et al., The Effect of Supplemental L-Arginine on Tolerance Development During Continuous Transdermal Nitroglycerin Therapy, J. of Am. Coll. of Cardiology, 39(7): 1199-1203, 2002.

(56) References Cited

OTHER PUBLICATIONS

PE Science High Volume advert from bodybuilding.com website, retrieved Aug. 23, 2016 from archive web: http://web. archive.org/web/20141107040448 30/http://pescience.com/highvolume.html, 5 pages, 2014.
Pellegrino, D., et al., "Nitrite exerts potent negative inotropy in the isolated heart via eNOS-independent nitric oxide generation and cGMP-PKG pathway activation", Biochilnica et Biophysica Acta, 1787:818-827, 2009.
PEScience High Volume, 2007. 2 pages.
Petersen, et al., "Nitrate and nitrite in vegetables on the Danish market: content and intake", Food Additives and Contaminants. 16(7):2910299, 1999.
Petersson et al., "Dietary nitrate increases gastric mucosal blood flow and mucosal defense," Am. J. Physiol. Gastrointest. Liver, 292: G718-G724, 2007.
Petrosyan et al, "L-Histidine nitrates", Journal of Molecular Structure, 2006. p. 160-167 vol. 794. www.sciencedirect.com.
Piccolo et al. CAS: 138: 1375892003. 3 pages, 2014.
Pickering et al., Why Don't We Use Nitrates to Treat Older Hypertensive Patients?, Journal of Clinical Hypertension, vol. 7, No. 11, pp. 685-690 (Nov. 2005).
Pischel et al. CAS: 134:71896, 2001. 1 page.
Poderoso et al., "Nitric Oxide Regulates Oxygen Uptake and Hydrogen Peroxide Release by the Isolated Beating Rat Heart", Am. J. Physiol. 274 (Cell Physlol. 43): C112-C119: 1998.
Pomerantz, DK. et al, "Nitric Oxide is a Mediator of the Inhibitory Effect of Activated Macrophages on Production of Androgen by the Leydig Cell of the Mouse", Endocrinology 139: 922-931, 1998.
Pomeranz, A., et al., "Elevated salt and nitrate levels in drinking water cause an increase of blood pressure in schoolchildren", Kidney Blood Press. Res. 23:400-403, 2000.
Posts from bodybuilding.com website re soon to be released PE Science High Volume supplement, retrieved Aug. 23, 2016 from web archive: http://forum.bodybuilding.com/showthread.php?t=164369241&highlight=PEScience+High+Volume, 2014.
Pradhan et al."Effect of Anions on the Solubility of Zwitterionic Amino Acids," J. Chem. Eng. Data 45(1):140-143 (2000).
Preston-Martin, S., et al., "Maternal consumption of cured meats and vitamins in relation to pediatric brain tumors", Cancer Epidemiology, Biomarkers & Prevention, 5:599-605, 1996.
ProArgi 9 Supplement Website: ProArgi-9 Plus FAQ, "ProArgi 9 Plus Site", http:// proargi9site.blogspot.eom/p/proargi-9-plus-faq.html, Apr. 22, 2014. 5 pages.
PS Nutrition Creatine Nitrate, on line, sale product, 2014. 5 pages.
"Amino acids: MedlinePlus Medical Encyclopedia", [online] retrieved on Mar. 27, 2025 from: https:/medlineplus.gov/ency/article/002222.html.
"Bodybuilding website posts of a test subject (Owen70) relating to effects of daily Arginine nitrate supplementation, pre-workout". 4 pages, 2007. Retrievable at https://forum.bodybuilding.com/showthread.php?t=3050561.
"Bodybuilding website posts of a test subject (soopamyko)", 29 pages, 2010.
"Bodybuilding website posts of a test subject (SShred32)", Retrievable at: https://forum.bodybuilding.com/showthread.php?t=3050561, 16 pages, 2010.
"Co-administration" Cambridge English Dictionary; [online] retrieved on Mar. 27, 2025 from: https://dictionary.cambridge.org/us/dictionary/ english/co-administration; 1 page. (Year: 2025).
"Coadministration" Collins English Dictionary; [online] retrieved on Mar. 27, 2025 from: https://www.collinsdictionary.com/us/dictionary/ english/coadministration; 1 page. (Year: 2025).
"Dietary Nitrate and Nitrite to Increase Nitric Oxide in Patients with Coronary Artery Disease," Clinical Trial available at http://clinicaltrials.gov/ct2/show/NCT00069654, 2010.
"Dietary reference intakes for energy, carbohydrate, fiber, fat, fatty acids, cholesterol, protein and amino acids." Chapter 10: Protein and Amino Acids. National Academy Press, Washington, DC. 2005.
"Dymatize Nutritional Supplements, Whey Protein, Bodybuilding & Weight Products", 2013 Dymatize Enterprises LLC, Xpand 2x36 Serving, http://www.dymatize.com/products/nitric-oxide/detail/1166/ xpand-2x-36-serving, 2013. 4 pages.
"Glyceryl trinitrate—leaflet print—Patient UK," available at http://www.patient.co.uk/printer.asp?dock=30003883, 2008.
"Heart attack—Nitrates & vasodilators—Revolution health," available at http://www.revolutionhealth.com/conditions/heart/heart-attack/medication-types/nitrates-vasodilators, 2011. 1 page.
"Isosorbide dinitrate—leaflet print—Patient UK," available at http://www.patient.co.uk/printer.asp?doc=30003884, 2011.
"Isosorbide mononitrate-leaflet print—Patient UK," available at http://www.patient.co.uk/printer.asp?doc=30003885, 2008.
"Juice box", https://web.archive.org/web/20051123042314/http:// www.madehow.com/voume7/juice-box.html, Retrieved Mar. 2006.
"Nitrates and nitrites (PIM G016)," available at http://inchem.org/documents/pims/chemical/img016.htm, retrieved online Mar. 23, 2011.
"Nitrates and Nitrites", TEACH Chemical Summary, U.S. EPA, Toxicity and Exposure Assessment for Children's Health, published by the U.S. Environmental Protection Agency on May 22, 2007 (Year: 2007). 15 pages.
"Pharmaceutical Manufacturing", in Remington: The Science and Practice of Pharmacy, 21st ed. 1889, 2006. pp. 732-744, 889-928, 1690-1692.
"Prudent Practices in the Laboratory: Handling and Disposal of Chemicals", National Academy Press, Washington, DC, pp. 198-199, 1995.
"Scientific and Technical Assessment Report on Nitrosamines," 1977 US Environmental Protection Agency (EPA) Office of Research and Development: EPA-600/6-77-001, Jun. 1977.
"Solaray—Beet root.", Retrieved from http://web/archive/org/web/20060521193831/http://www.nutraceutical.com/search/view_product.cfm?product_index=7661441, May 14, 2007.
"Survey of nitrates and nitrites in food and beverages in Australia", Food Standards, Australia and New Zealand, undated.
"Xpand 2x by Dymatize at Bodybuilding.com—Lowest Price on Xpand 2x!", Advertisement, 2012 BodyBuilding.com, LLC, http://www.bodybuilding.com/store/dymatize/xpand-2x.html, Jun. 8, 2013. 5 pages.
21 CFR 101.12, "Reference Amounts Customarily Consumed Per Eating Occasion", 4-1-3 edition, 2003.
21 CFR 172.170 Sodium nitrate. Apr. 1, 2015. 3 pages.
21 CFR 172.372 N-acetyl-L-methionine. 2 pages, 2026.
A Butler et al., Medieval Chinese Medicine: The Dunhuang Medical Manuscripts (Chapter 16: A treatment for carenovascular dysfunction in a Dunhuang medical manuscript), Routledge (2005) 14 pages.
A. Patrician et al., "Dietary nitrate enhances arterial oxygen saturation after dynamic apnea", Scand J Med Sci Sports, (20170000), vol. 27, doi:10.1111/sms.12684, pp. 622-626, XP055943939.
Abd El-Gawad et al. AAPS PharmaSciTech, 2017, 18(5): 1795-1809.
Abel, et al., "Influence of Chronic Supplementation of Arginine Aspartate in Endurance Athletes on Performance and Substrate Metabolism: A Randomized, Double-Blind, Placebo-Controlled Study", Int J Sports Med, 26: 344-349, 2005.
Abou-Mohamed et al. "Role of L-Arginine in the Vascular Actions and Development of Tolerance to Nitroglycerin", British Journal of Pharmacology (2000) 130, 211-218.
Acetyl/propionyl Carnitine from BodyBuilding, 2006.1 page.
Ahtee et al."Taurine Biological Actions and Clinical Perspectives," J. Nutr. 116:2555-2556 (1986).
Alvarez Roger A. et al: "Home Nitric Oxide Therapy for COVID-19", American Journal of Respiratory and Critical Care Medicine, vol. 202, No. 1, Jul. 1, 2020 (Jul. 1, 2020), pp. 16-20, XP093325276, ISSN: 1073-449X, DOI: 10.1164/rccm.202005-1906ED.
Am. Chem. Soc., Chemical abstracts seventh collective. vols. 56-65, 1962-1966, Chq-Dib, © 1969, Index for creatine-related abstracts.
American Cancer Society, "What is stomach cancer?", website information, Sep. 2018.

(56) References Cited

OTHER PUBLICATIONS

Amidon, G. L. et al., "Intestinal Absoption of Amino Acid Derivatives: Structural Requirements for Membrane Hydrolysis.", Journal of Pharmaceutical Sciences., (1983), vol. 72, No. 8, pp. 943-944, XP055127041.
Amino Thrust dietary supplement, 2007. 2 pages.
Anders et al. "Aminoacylases", 1994, Advances in Pharmacology, vol. 27, pp. 431-448. (Year: 1994).
Anderson, K. "Nitrate and Nitrite in Human Nutrition" The Graduate College in the University of Nebraska, Lincoln, Nebraska, 1982. 160 pages.
Aniya et al., "Evaluation of Nitric Oxide Formation from Nitrates in Pig Coronary Arteries," Jpn. J. Pharmacol. 71:101-107 (1996).
Anonymous: "Nitric oxide", Nov. 2, 2020 (Nov. 2, 2020), XP093325297, Retrieved from the Internet: URL:https://en.wikipedia.org/w/index.php?title=Nitric_oxide&oldid=986690656.
Appel et al. "A Clinical Trial of the Effects of Dietary Patterns on Blood Pressure" The New Englad Journal of Medicine, vol. 336, No. 16; pp. 1117-1124 (Apr. 17, 1997).
Archer, Douglas L., Evidence that Ingested Nitrate and Nitrite Are Beneficial to Health, Journal of Food Protection, vol. 65, No. 5, pp. 872-875 (2002).
Arenas et al., "Carnitine in muscle, serum, and urine of nonprofessional athletes: Effects of physical exercise, training, and L-carnitine administration" Muscle & Nerve, 1991, 14:598-604.
Arenas-Valganon, J., et al., "Taurine-nitrite interaction as a precursor of alkylation mechanisms", Food Chem. 134:986-991, 2012.
Armstrong, L., et al., "Influence of diuretic-induced dehydration on competitive running performance", Med. Sci. Sports Exercise. 17(4):456-461, 1985.
Arnold et al., "Reversible and irreversible hemichrome generation by the oxygenation of nitrosylmyoglobin" Biochemistry, 1999, 38: 4750-4756.
Arnold Iron CRE3, 2007. 1 page.
Arnold Schwarzenegger website announcement (2013-2014): "Arnold Teams With Musclepharm to Develop the Arnold Series Line of Nutritional Supplements", retrieved from schwarzenegger.com on Aug. 23, 2016, 3 pages.
Artioli et al. "Role of beta-Alanine Supplementation on Muscle Carnosine and Exercise Performance" Med. Sci. Sprots Exerc, Jun. 2010, vol. 42, No. 6pp. 1162-1173.
PubChem, Physical Description of Fluoroboric Acid, 1 page.
PubChem, Physical Description of Hexafluorophosphoric Acid, 1 page.
PubChem, Physical Description of Trifluoroacetic Acid, 1 page.
QuadraLean by RSP Nutrition, Bodybuilding.com, 2006. 1 page.
Que, R. et al., "A Simple, Facile Demonstration of Copper and Nitric Acid Reaction", Journal of Chemical Education. 2022, 99, 2762-2765.
Rajkumar et al., "Infrared and Raman spectra of DL-aspartic acid nitrate monohydrate," Spectrochimica Acta Part A, 54:1527-1532, 1998.
Rajkumar et al., "Infrared and Raman spectra of L-valine nitrate and L-leucine nitrate," J. Raman Spectrosc. 51:1107-1112(2000).
Ramaswamy et al., "L-ornithine nitrate", Acta Cryst., E58, 646-648 (2002).
Ramaswamy et al., "Vibrational Spectroscopic Studies of L-argininium dinitrate"Journal of Raman Spectroscopy 2003. p. 50-56. vol. 34. www.interscience.wiley.com.
Ramberg, Peter J. "Paper tools and fictional worlds: Prediction, synthesis and auxiliary hypotheses in chemistry.", Tools and modes of representation in the laboratory sciences. Dordrecht: Springer Netherlands, 2001. 61-78.
Rankin J. et al, "The Effect of Oral Arginine During Energy Restriction in Male Weight Trainers", Journal of Strength and Conditioning Research, 8(3), 170-177, 1994.
Rao et al."Structure and Conformational Aspects of the Nitrates of Amino Acids and Peptides. I. Crystal Structure of Glycylglycine Nitrate," Acta Cryst. B29:2379-2388 (1973).
Raymond et al., "Effects of Acute Red Spinach Extract Ingestion on Repeated Sprint Performance in Division I NCAA Female Soccer Athletes." (Oxygen 2023;3:133-142). (Year: 2023).
Redibeets website: https: //web/archive.org/web/20060206221752/https://allonhealth.com/health-products/redibeets.htm, 2006.
Results of a US Patent and Trademark Office (USPTO) Patent Trial and Appeal Board (PTAB) Institutions Search showing Thermolife International related PTAB and Federal civil litigation matters, 2011-2025, as of Feb. 24, 2026. 6 pages.
Richardson et al., "The ingestion of inorganic nitrate increases gastric S-nitrosothiol levels and inhibits platelet function in humans", Nitric Oxide, 7:24-29, 2002.
Riens et al., "Amino Acid and Sucrose Content Determined in the Cytosolic, Chloroplastic, and Vacuolar Compartments and in the Phloem Sap of Spinach Leavesl", Plant Physiol. (1991) 97, 227-233, Apr. 6, 1991.
Rimando et al., "Determination of Citrulline in Watermelon Rind", Journal of Chromatography A, 1078 (2005) 196-200, May 2, 2005.
Rizzi, G.P., "Role of Phosphate and Carboxylate Ions in Maillard Browning", Journal of Agricultural and Food Chemistry 52(4):953-957, 2004.
Rocke, AJ., "Chemical Atomism in the Nineteenth Century: From Dalton to Cannizzaro", Columbus: Ohio State University Press, 1984. ISBN 0-8142-0360-4.
Rombauer, Irma S., "Joy of Cooking", 75th Anniversary, Scribner, New York, 2006, p. 163 (2006).
Romero et al."Therapeutic Use of Citrulline in Cardiovascular Disease," Cardiovascular Drug Reviews 24(3-4):275-290 (2006).
Rosen et al. "Nutrient Management for Commercial Fruit & Vegetable Crops in Minnesota" University of Minnesota extension Service, 2005 pp. 35-36 <https://conservancy.umn.edu/bitstream/handle/11299/51272/5886.pdf?sequence=1>.
Roy, et al., "Insulin stimulation of glucose uptake in skeletal muscles and adipose tissues in vivo is No. dependent", Am. J. Physiol. Endocrinol. Metabol. 274(4):E692-699, 1998.
RSPReGenBCAA, 2006. 2 pages.
Rudnic, Schwartz, "Oral solid dosage forms", in Remington: The Science and Practice of Pharmacy, 2:1618-1619, 2000.
Ruel et al., "Concomitant treatment with oral L-arginine improves the efficacy of surgical angiogenesis in patients with severe diffuse coronary artery disease: The Endothelial Modulation in Angiogenic Therapy randomized controlled trial", J Thorac Cardiovasc Surg 135:762-770 (2008).
Russel, C.A., "The History of Valency", History of Science 11(1): 53, 1973.
Rytlewski et al., "Effects of oral L-arginine on the pulsatility indices of umbilical artery and middle cerebral artery in preterm labor," European Journal of Obstetrics &Gynecology and Reproductive Biology 138:23-28 (2008).
Rytlewski et al."Effects of prolonged oral supplementation with L-arginine on blood pressure and nitric oxide synthesis in preeclampsia," Eur J Clin Invest 35(1):32-37 (2005).
Sader et al., "Endothelial Function, Vascular Reactivity and Gender Differences in the Cardiovascular System", Cardiovascular Research 53 (2002) 597-604, Aug. 21, 2001.
Sale et al. Effect of beta-alanine supplementation on muscle carnosine concentrations and exercise performance. Amino Acids, 39:321-333, 2010.
San Corporation dietary supplement containing creatine nitrate, 2006. 1 page.
Sanchez-Echaniz, J., et al. "Methemoglobinemia and consumption of vegetables in infants", Pediatrics, vol. 107., No. 5, May 2001.
Santamaria et al. "A survey of nitrate and oxalate content in fresh vegetables" Journal of the Science of Food and Agriculture, 1999, vol. 79, 1882-1888. (Year: 1999).
Santamaria, J., Nitrate in vegetables: toxicity, content, intake and EC regulation, Journal of the Science of Food and Agriculture, 86:10-17 (2006).
Sar et al., "Effects of Combination of Nitrate with beta1-4 Galacto-oligosaccharides and Yeast on Methane Emission from Sheep", Asian-Aust. J. Anim. Sci., vol. 17, No. 1:73-79, 2004.

(56) References Cited

OTHER PUBLICATIONS

Sarasua S., and Savitz, D., "Cured and broiled meat consumption in relation to childhood cancer: Denver, Colorado (United States)", Cancer Causes and Control. 5:141-148, 1994.
Sastre et al., "Metabolism of agmatine in macrophages: modulation by lipopolysaccharide and inhibitory cytokines," Biochem. J. 330:1405-1409 (1998).
Sawka, M., "Physiological consequences of hypohydration: exercise performance and thermoregulation", Med. Sci. Sports Exercise. 24(6):657-670, 1992.
Scardi, "Chronic Treatment After Acute Myocardial Infarction: VVhich Drug for Which Patient?", Nitrates, Journal of Cardiovascular Pharmacology 14 (Suppl. 9):S84-888, 1989.
Schaefer et al., "L-Arginine Reduces Exercise-Induced Increase in Plasma Lactate and Ammonia", Inti. J. of Sports Medicine, 2002,23(6):403-407.
Schulbach et. al., "Guide to nitrogen quick-tests for vegetables wit the 'cardy' nitrate meter" FREP Contract #95/0582. 11 pages.
Schulz et al., "Functional and Biochecical analysis of Endothelial (Dys)function and NO/cGMP Signaling in Human Blood Vessels with and Without Nitroglycerin Pretreatment," Circulation 105:1170-1175 (2002).
Schwedhelm et al., "Pharmacokinetic and Pharmacodynamics properties of oral L-citrulline and L-arginine: impact on lithe oxide metabolism," Br J Clin Pharmacol 65(1):51-59 (2007).
Sen et al. Journal of Association of Official Analytical Chemists, 61(6): 1389-1394, 1978.
Sheiner et al., "Pharmacokinetic/Pharmacodynamic Modeling in Drug Development", Annu. Rev. Pharmacol. Toxicol., vol. 49, pp. 67-95. 2000.
Shen et al., "Endogenous nitric oxide in the control of skeletal muscle oxygen extraction during exercise", Acta Physiol. Scand, 2000, 168(4): 675-686.
Shen et al., "Nitric oxide production and NO synthase gene expression contribute to vascular regulation during exercise.", Med Sci Sports Exerc, 27(8):1125-34, 1995.
Shephard, S.E., et al., "Assessment of the risk of formation of carcinogenic N-nitroso compounds from dietary precursors in the stomach", Food Chem. Toxic. 25(1):91-108, 1987.
Fetih et al., "Nitric oxide donors can enhance the intestinal transport and absorption of insulin and [Asu1,7]-eel Calcitonin in rats," Journal of Controlled Release 106:587-297 (2005).
Fetih et al."Excellent Absorption Enhancing Characteristics of NO Donors for Improving the Intestinal Absorption of Poorly Absorbable Compund Compared with Conventional Absorption Enhancers," Drug Metab. Pharmacokinet. 21(3):222-229 (2006).
Flaherty,"Nitrate tolerance a review of the evidence," Johns Hopkins University School of Medicine, Drugs, 37:523-550, 1989.
Fleck, M., & Petrosyan, AM., "Salts of amino acids. Crystallization, Structure and Properties", Cham, Switzerland: Springer International Publishing, 10:978-83, 2014.
Food and Agriculture Organization, Technology of production of edible flours and protein products from soybeans, Chapter 1, "The Soybean", pp. 1-12, publ. Jan. 31, 2001 (Year: 2001).
Franciosa and Cohn, "Effect of Isosorbide Dinitrate on Response to Submaximal and Maximal Exercise inPatients With Congestive Heart Failure", Am J Cardiol, 143(5):1009-1014; 1979.
Franciosa et al., "Contrasting immediate and long-term effects of isosorbide dinitrate on exercise capacity in congestive heart failure," Am J Med 69( 4):559-566, 1980.
Fraser et al., "Physical fitness and blood pressure in school children," Circulation, vol. 67 No. 2, 405-412, 1983.
Fregly, M., "Effect of hypertonic sodium nitrate solutions on blood pressure of rats", Proc. Soc. Exper. Biol. Med. 115(2), 386-391, 1964.
Fryar, et al., "Mean Body Weight, Height, Waist Circumference and Body Mass Index Among Adults: US: 1999-2000 through 2015-2016", National Health Statistics Report No. 122, Dec. 20, 2018.
G. M. McKnight, et al., Chemical synthesis of nitric oxide in the stomachfi-om dietary nitrate in humans, Gut, vol. 40, pp. 211-214 (1997).
Gago et al., Red wine-dependent reduction of nitrite to nitric oxide in the stomach, Free Radical Biology and Medicine 43:1233-1242, 2007. 10 pages.
Galachiev S.M. et al: Possibilities of endogenous formation of nitrosamines in gastric juice In Vitro, Samara Scientific Center of the Russian Academy of Sciences Bulletin, 2011, vol. 13, No. 1(7), pp. 1678-1680.
Gallaher and Scheeman, "Effect of dietary fiber on protein digestibility and utilization", in CRC Handbook of dietary fiber in human nutrition, GA Spiller, ed., 3rd edition. CRC Press, Boca Raton, FL, Chapter 4.1, pp. 133-160, 2001. ISBN 0-8493-2387-8.
Gao et al., "Agmatine: A Novel Endogenous Vasodilator Substance," Life Sciences, 57(8):83-86, 1995.
Gao, X., et al., "NADPH Oxidase in the Renal Microvasculature Is a Primary Target for Blood Pressure lowering-effects by Inorganic Nitrate and Nitrite", Hypertension. 65:161-170, 2015, DOI:1161/HYPERTENSIONAHA.114.04222.
George Barger, M.A., D.Sc., "The Simpler Natural Bases", Monographs on Biochemistry, U.C.D. Library, Nov. 23, 1960, Digitized 2007. 232 pages.
Giant Sport Metabolic Bioshock—Workout Supplement, on line, sale product, 2014. 1 page.
Gibson et al. "Protective role of the epithelium of the small intestine and colon", Inflamm. Bowel Dis., 1996, vol. 2, No. 1, pp. 279-302, abstract provided. (Year 1996).
Gmelin, L., "Handbook of Chemistry", (vol. 5), H. Watts (translator), pp. 249-255, 1861.
GNC Mega Men, "GNC Mega Men 90 Caplets", http://www.gnc.com/GNC-Mega-Men-reg/ product.jsp?productId=4033432, Apr. 22, 2014. 3 pages.
Godzisz, "Classification and nature of hydrogen bonds to betaine. X-ray, 13C CP MAS and IR description of low barriei hydrogen bonds," Journal of Molecular Structure, 606:123-137,2002.
Gonzalez-Alonso, J., et al., "Muscle blood flow is reduced with dehydration during prolonged exercise in humans", J. Physiol. 513(3):895-905, 1998.
Gonzalez, "Migraines Are Correlated with Higher Levels of Nitrate-, Nitrite-, and Nitric Oxide-Reducing Oral Microbes in the American Gut Project Cohort". mSystems. Oct. 18, 2016; 1(5): e00105-16. doi: 10.1128/mSystems.00105-16. Erratum in: mSystems. ( Year: 2016) 4 pages.
Grasemann et al., "Oral L-arginine supplementation in cystic fibrosis patients: a placebo-controlled study," Eur Respir J 25:62-68 (2005).
Green et al., "Control of Skeletal Muscle Blood Flow During Dynamic Exercise", Sports Med., 1996, 21(2): 119-146.
Green, et al., "Nitrate biosynthesis in man", PNAS 78(12):7764-7768, Dec. 1981.
Gui, Iai et al., "Reduction of N-Nitrosodimethylamine with Granular Iron and Nickel-Enhanced Iron. 1. Pathways and Kinetics", Environmental Science & Technology, vol. 34, No. 16, Jul. 14, 2000, pp. 3489-3494.
Gwartney, "On the Horizon: A Glimpse into the Future of Supplementation," in Pump magazine, Nov./Dec. (Year: 1998) 4 pages.
Gwartney, D. L, "On the Horizon: Agmatine," Oct./Nov. 1998, PUMP 101:96-97.
H. Yamasaki, "Blood nitrate and nitrite modulating nitric oxide bioavailability: potential therapeutic functions in COVID-19", Nitric Oxide, vol. 103, doi:https://doi.org/10.1016/j.niox. 2020.07.00 5, (JUl. 23, 2020), pp. 29-30, XP055943941.
Hambrecht, et al., "Correction of endothelial dysfunction in chronic heart failure: additional effects of exercise training and oral L-arginine supplementation", J Am College Cardiol, 35(3):706-713, 2000.
Han Ying et al., "Reduction of N-Nitrosodimethylamine with zero-valent zinc", Water Research, vol. 47, No. 1, Jan. 1, 2013 (Jan. 1, 2013), pp. 216-224, XP093221894, Amsterdam, NL ISSN: 0043-1354, DOI: 10.1016/j.watres.2012.09.043.

(56) References Cited

OTHER PUBLICATIONS

Hanson et. al., "Biosynthesis, Translocation, and Accumulation of Betaine in Sugar Beet and Its Progenitors in Relation to Salinity" Plant Physiol., vol. 70, pp. 1191-1198, publ. 1982 (Year: 1982).
Harris et al. "The absorption of orally supplied beta-alanine and its effect on muscle carnosine synthesis in human vastus lateralis" Amino Acids, 2006, vol. 30, pp. 270-289. (Year: 2006).
Harris, R.C., "The Influence of Beta-Alanine Supplementation and Training on the Muscle Carnosine Content in Human v. lateralis, and the Effect of This on Exercise Performance," Amino Acids 29:12-13 (2005).
Harrison, D.G. et al., "The Nitrovasodilators, new Ideas About Old Drugs," Circulation, vol. 87, No. 5, May 1993, pp. 1461-1467).
Hatanaka et al., "Stereoselective Pharmacokinetics and Pharmacodynamics of Organic Nitrates in Rats," Journal of Pharmacology and Experimental Therapeutics 298:346-353 (2001).
Haussuhl, "Elastic and thermoelastic properties of twelve adducts of betaine," Z Kristallogr, 188:311-320, 1989.
Hayashi et al., "L-citrulline and L-arginine supplementation retards the progression of high-cholesterol-diet-induced atherosclerosis in rabbits," PNAS 102(38): 13681-13686 (2005).
Henriksson et al., "Dietary nitrate lowers oxygen cost during exercise.", Acta Physiol, Sep. 1, 2007, 191:1. 1 page.
Henry, et al., "Free amino acid, ammonium and nitrate concentrations in soil solutions of a grazed coastal marsh in relation to plant growth", Plant, Cell and Environment. 25:665-75, 2002.
Herbwisdom.com, 2006. 4 pages.
Heusch et al., "Endogenous Nitric Oxide and Myocardial Adaptation to Ischemla", Circ. Res. 2000; 87: 146-152, 2000.
Hiatt, E., "Comparison of the diuretic effects of nitrate salts with other diuretic agents", Am. J. Physiol., 189(1):173-176, 1957.
Hickner, et al., "Role of nitric oxide in skeletal muscle blood flow at rest and during dynamic exercise in humans", Am J Physiol: Heart Circ Physiol., 42: H405-H410, 1997.
Hoffman et al., "Effect of Creatine and p-Alanine Supplementation on Performance and Endocrine Responses in Strength/Power Athletes", International Journal of Sport Nutrition and Exercise Metabolism, 2006, 16, 430-446, © 2006 Human Kinetics, Inc.—20.
Honikel, K., "The use and control of nitrate and nitrite for the processing of meat products", Meat Science, 2008,78:68-76.
Hord et al., "Food Sources of Nitrates and Nitrites: The Physiological Context for Potential Health Benefits," Am. J. Clin. Nutr. 90:1-10, 2009.
Declaration of Richard Chamberlain under 37 CFR 1.132, Aug. 28, 2014, Filed in reexam, control Nos. U.S. Appl. No. 90/011,869 and U.S. Appl. No. 90/011,869 11 pages.
Declaration of Richard Chamberlain under 37 CFR 1.132, Mar. 30, 2016, Filed in reexam, control Nos. U.S. Appl. No. 90/011,869 and U.S. Appl. No. 90/011,869, 20 pages.
Declaration of Ron Kramer and Alex Nikolaidis under 37 CFR 1.132, Apr. 29, 2019, submitted in U.S. Appl. No. 14/065,371.
Declaration of Trevor H. Levere under 37 FR 1.132, Mar. 29, 2016.
Deeb, B., and Sloan K.. "Nitrates, Nitrites, and Health, Bulletin 750", (Abstract), Eric No. ED152512, May 1975. 2 pages., https://eric.ed.gov/?id=ED152512.
Definitions for "diluent" and "excipient" from Stedman's Medical Dictionary for the Health Professions and Nursing (illustrated), 5th ed. Lippincott Williams and Wilkins, Philadelphia, PA, 3 pages.
Deighton, "How Snapple got its juice back", Harvard Business Review R0201—Jan. 2002.
Del Compo et al., "Creatinine, creatine and protein in cooked meat products", Food Chemistry, vol. 63, No. 2, pp. 187Y190, 1998.
Del Pilar Garcia-Santos et al., "Reactivity of Amino Acids in Nitrosation Reactions and Its Relation to the Alkylating Potential of Their Products," J. Am. Chem. Soc, 2002, 124(10): 2177-2182.
Dessaignes, "Scientific and Medicinal Chemistry. Examination of some products by the transformation of creatine" Comptes Rendus, No. 19, May 8, 1854 (reprinted as "Research on Some Products of the Transformation of Creatine," The Chemist—A Monthly Journal, vol. 1, Samual Highley Publishers, London, 1854, pp. 594-597).
Dhar et al., Complex Compounds of Acid, Base and Salt with Nitrogenous and Other Organic Substances, in National Academy of Sciences, India, Symposium on Nitrogen, Part 1, Section A, vol. 31,1961, pp. 76-79.
Dhas, S.A. Martin Britto et al., Growth and Characterization of a New Organic NLO Material; Glycine Nitrate, ScienceDirect, Optics communications 278 (2007) 434-438.
Di Pasquale, Amino Acids and Proteins for the Athlete: The Anabolic Edge, 1st Edition, 1997, pp. 99-153.
Di Prampero, PE., "An Analysis of the Factors Limiting Maximal Oxygen Consumption in Healthy Subjects", Chest 101 (5 supplement):188S-191S, May 1992.
Do Amaral Angélica et al: "The effect of acute magnesium loading on the maximal exercise performance of stable chronic obstructive pulmonary disease patients", Clinics, vol. 67, No. 6, Jun. 1, 2012 (Jun. 1, 2012), pp. 615-621, XP093325270, BR ISSN: 1807-5932, DOI: 10.6061/clinics/2012(06)12.
Drewett, JG. et al, "Nitric Oxide Potently Inhibits the Rate-Limiting Enzymatic Step in Steroidogenesis", Mol Cell Endocrinol., Aug. 30, 2002, 194(1-2):39-50.
Duncan et al., "Chemical generation of nitric oxide in the mouth from the enterosaliary circulation of dietary nitrate," Nature Medicine, 1 (6): 546-551, Jun. 1995.
Duncker et al., "Nitric oxide contributes to the regulation of vasomotor tone but does not modulate O2-consumption in exercising swine", Cardiovasc Res, 47:738-748, 2000.
Dymatize Nutrition, "Pre-Workout", http://www.dymatize.com/nitric-oxide, Mar. 31, 2014- Advertisement. 1 page.
Dymatize Nutrition, "Xpand 2x 10 Serving-Dymatize Nutritional Supplements, Whey Protein, Bodybuilding", http://www.dymatize.com/store/p/289-Xpand-2x-10-Servings.html—Advertisement. 2 pages.
Dymatize® Xpand 2x®, Fruit Punch, Dymatize GNC, www.gnc.com/product/index.jsp?productId=13180805, Jun. 13, 2013. 4 pages.
Dymatize® Xpand 2x®, Fruit Punch, Dymatize-GNC, www.gnc.com/product/index.jsp?productId=13180805, Jun. 17, 2013, p. 1.
Dymkowska-Malesa M. et al., "Content of nitrates (V) and nitrites (III) in some vegetables grown in the region of Warmia and Mazury", (Abstract), Rocz Panstw Zakl Hig, 57(2):125-131, 2006.
EAS advertisement for "Phosphagen Elite" Joe Weider's Muscle & Fitness, Sep. 2005. 2 pages.
Eaton et al., "Urinary Beta-Alanine Excretion is a Marker of Abnormal as well as Normal Gut Fermentation", Journal of Nutritional & Environmental Medicine (Jun. 2004) 14(2), 121-127.
Edmunds C. and Cushny, A., "Laboratory Guide in Experimental Pharmacology", George Wahr, Ann Arbor, MI, pp. 239-244, 1918.
Edwards et al., "Cysteine, Tyrosine and Essential Amino Acid Contents of Selected Foods," Amino Acids in Foods, Journal of Agriculture and Food Chemistry, 3(11):952-957, 1955,.
Elam, et al., "Effects of arginine and ornithine on strength, lean body mass and urinary hyroxyproline in adult males", J. Sports Med. Phys. Fitness. 29(1):52-56, https://www.pubmed.ncbi.nlm.nih. gov/2770269/, 1989.
Elkayam et al. "Prevention of nitrate tolerance with concomitant administration of hydralzaine" Can J CArdiol, 1996, vol. 12, suppl C, pp. 17C-21C. (Year 1996).
Elmore et al., "Compilation of free amino acid data for various food raw materials, showing the relative contributions of asparagine, glutamine, aspartic acid and glutamic acid to the fee amino acid composition", Oct. 2002, JIFSAN Acrylamide in Food Workshop, Chicago. (Year 2002). 3 pages.
Endo, et al. "Role of nitric oxide in exercise-induced vasodilation of the forearm" Circulation. 90:2886-2890, 1994.
Endo, H., et al., "Screening of compounds structurally and functionally related to N-methyl-N'-nitro-N-nitrosoguanidine a gastric carcinogen", GANN 65:45-54, Feb. 1974.
English translation of foreign Croatian patent HRP20140504 A2; Dec. 4, 2015, 24 pages.
English translation of KR-20110015141-A, Feb. 15, 2011, pp. 1-23 (Year: 2011).
Eppendorfer et al., "Free and Total Amino Acid Compositions of Edible Parts of Beans, Kale, Spinach, Cauliflower and Potatoes as influenced by Nitrogen," Journal of Science of Food and Agriculture, 71:449-458, 1996.

(56) References Cited

OTHER PUBLICATIONS

Eskiocak S. et al., "The Effects of Taking Chronic Nitrate by Drinking Water on Thyroid Functions and Morphology", Clin Exp Med., Jul. 2005, 5(2):66-71.
Eto et al. "Glutamate-arginine salts and hormonal responses to exercise" Archives of Physiology and Biochemistry, 1995, 103 (2):160-164.
European Commission, "Reports of the Scientific Committee for Food (1992): Opinion of the Scientific Committee for Food on: Nitrates and Nitrite", Oct. 1990, 14 pages.
Examine.com, "L-Carnitine", Sep. 12, 2014, https://examine.com/supplements/l-carnitine/. (Year:2014) 36 pages.
Expert Declaration of Dr. Richard Chamberlain in support of Plaintiffs' Opposition to Defendant's Motion for Summary Judgment in *Thermolife Int'l* v. *Redefine Nutrition*, Master Case CV13-03630 GAF (FFMx), Nov. 18, 2013.
F. Murad, Cyclic Guanosine Monophosphate as a Mediator of Vasodilation, J. Clin. Invest., vol. 78, pp. 1-5 (Jul. 1986).
F. Ray, Meat Curing, ANSI-3994, OSU, 3 pages. Date unknown.
Fanous, S. "Is Sodium Nitrate Bad for You?", May 20, 2015, Healthline, https://www.healthline.com/health/food-iuthtion/is-sodium-nitrate-bad-for-you#1, pp. 1-8. (Year: 2015).
Fayers et al."Nitrate tolerance and the links with endothelial dysfunction and oxidative stress," Br J Clin Pharmacol 56:620-628 (2003).
FDA 21 C.F.R. (I)(B) §§ 172.160 and 172.170, revised Apr. 1, 2018 (Year: 2018). 12 pages.
FDA basics: "What is a dietary supplement?", Retrieved Aug. 23, 2016 from www.fda/gov/aboutfda/transparncy/basics/ucm195635.html.
FDA Regulation 42 FR, 1977, 52 pages.
FDA Regulation 48 FR 1701, Indirect Food Additives; Paper and Paperboard Components, FDA, 1983, 5 pages.
Feelisch et al., Eur J. Pharmacol., 1987, 139(1): 19-30.
Ferrari, G. et al., "The application of high hydrostatic pressure for the stabilization of functional foods: pomegranate juice", J. Food Engineering, 100:245-253, Apr. 2010.
Harrison et al. ("General techniques of cell culture", Cambridge Press 1997, 162 pages).

* cited by examiner

AMINO ACID COMPOSITIONS

CROSS REFERENCE TO RELATED APPLICATIONS

This application is a continuation application of the earlier U.S. Utility patent application Ser. No. 19/030,516 to Ronald Kramer, et al. entitled "Amino Acid Compositions" filed Jan. 17, 2025, which is a continuation application of the earlier U.S. Utility patent application Ser. No. 17/522,680 to Ronald Kramer, et al. entitled "Amino Acid Compositions" filed Nov. 9, 2021, now issued as U.S. Pat. No. 12,227,483, which is a divisional application of the earlier U.S. Utility patent application Ser. No. 14/621,738 to Ronald Kramer, et al. entitled "Amino Acid Compositions" filed Feb. 13, 2015, now issued as U.S. Pat. No. 11,166,979, which is a continuation application of the earlier U.S. Utility patent application Ser. No. 13/920,066 to Ronald Kramer, et. al. entitled "Amino Acid Compositions" filed Jun. 17, 2013, now issued as U.S. Pat. No. 8,957,100, which is a continuation of the earlier U.S. Utility patent application Ser. No. 13/038,615 to Ronald Kramer, et. al. entitled "Amino Acid Compositions" filed Mar. 2, 2011, now issued as U.S. Pat. No. 8,466,187, which is a continuation-in-part of the earlier U.S. Utility patent application Ser. No. 12/336,938 to Ronald Kramer, et. al. entitled "Amino Acid Compositions" filed Dec. 17, 2008, now issued as U.S. Pat. No. 8,034,836, which is a continuation of the earlier U.S. Utility patent application Ser. No. 11/950,273 to Ronald Kramer, et. al. entitled "Amino Acid Compounds" filed Dec. 4, 2007, now issued as U.S. Pat. No. 7,777,074, which claims the benefit to U.S. Provisional Application No. 60/973,229 to Ronald Kramer, et al. filed Sep. 18, 2007, the disclosures of all of which are hereby incorporated entirely herein by reference.

BACKGROUND

Technical Field

Aspects of this document relate generally to amino acid compositions.

Background

It is desirable to design new amino acid compositions that have properties lacking in conventional amino acids, conventional nitrates, and conventional nitrites alone.

SUMMARY

Aspects of the disclosure relate to a solid supplement composition comprising at least one non-ester nitrate compound and at least one isolated amino acid compound, wherein the at least one isolated amino acid compound is creatine, wherein the at least one isolated amino acid compound is a separate compound than the at least one non-ester nitrate compound, and wherein the solid supplement composition comprises an amount of nitrate ion ($NO_3$—) that is at least 0.33125 mg.

Particular embodiments may comprise one or more of the following features.

The solid supplement composition may be in the form of powder and the amount of nitrate ion ($NO_3$—) may be at least 1 mg.

The solid supplement composition may be in the form of gel and the amount of nitrate ion ($NO_3$—) may be at least 1 mg.

The solid supplement composition may be in the form of powder and the amount of nitrate ion ($NO_3$—) may be at least 7 mg.

The solid supplement composition may be in the form of gel and the amount of nitrate ion ($NO_3$—) may be at least 5 mg.

The solid supplement composition may be in the form of powder and the amount of nitrate ion ($NO_3$—) may be at least 160 mg.

The solid supplement composition may be in the form of powder, the amount of nitrate ion ($NO_3$—) may be at least 7 mg, and the solid supplement composition may comprise beetroot, spinach, carrot, broccoli, and mushroom.

The solid supplement composition may be in the form of powder, the amount of nitrate ion ($NO_3$—) may be at least 160 mg, and the solid supplement composition may comprise beetroot, spinach, carrot, broccoli, and mushroom.

The solid supplement composition may comprise at least one component that is ion-exchange resin-based.

The solid supplement composition may be in the form of powder or gel, the amount of nitrate ion ($NO_3$—) may be at least about 1 mg, and the solid supplement composition may comprise an antioxidant.

The solid supplement composition may be in the form of powder, the amount of nitrate ion ($NO_3$—) may be at least about 1 mg, and the solid supplement composition may comprise citric acid, wherein the citric acid is from a separate source than the isolated amino acid compound and the at least one non-ester nitrate compound.

The solid supplement composition may be in the form of powder or gel, the amount of nitrate ion ($NO_3$—) may be at least about 1 mg, and the solid supplement composition may comprise three or more of the following: beetroot, spinach, rocket, carrot, broccoli, cabbage, and mushroom.

The solid supplement composition may be in the form of powder or gel, the amount of nitrate ion ($NO_3$—) may be at least about 1 mg, and the solid supplement composition may comprise four or more of the following: beetroot, spinach, rocket, carrot, broccoli, cabbage, and mushroom.

The solid supplement composition may be in the form of powder or gel, the amount of nitrate ion ($NO_3$—) may be at least about 1 mg, and the solid supplement composition may comprise five or more of the following: beetroot, spinach, rocket, carrot, broccoli, cabbage, and mushroom.

The solid supplement composition may be in the form of powder or gel, the amount of nitrate ion ($NO_3$—) may be at least about 1 mg, and the solid supplement composition may comprise a botanical nitrate source, a vegetable nitrate source, and an antioxidant.

The solid supplement composition may be in the form of powder or gel, the amount of nitrate ion ($NO_3$—) may be at least about 1 mg, and the solid supplement composition may comprise beetroot and an antioxidant.

The solid supplement composition may be in the form of powder or gel, and the solid supplement composition may comprise at least one isolated amino acid compound selected from: aspartic acid, proline, glycine, valine, agmatine, norvaline, ornithine, and arginine.

The solid supplement composition may be in the form of powder or gel, the amount of nitrate ion ($NO_3$—) may be at least 7 mg, and the solid supplement composition may comprise at least one isolated amino acid compound selected from: aspartic acid, proline, glycine, valine, agmatine, norvaline, ornithine, and arginine.

The solid supplement composition may be in the form of powder or gel, and the solid supplement composition may comprise at least two isolated amino acid compounds selected from: aspartic acid, proline, glycine, valine, agmatine, norvaline, ornithine, and arginine.

The solid supplement composition may be in the form of powder or gel, the amount of nitrate ion ($NO_3$—) may be at least 7 mg, and the solid supplement composition may comprise at least two isolated amino acid compounds selected from: aspartic acid, proline, glycine, valine, agmatine, norvaline, ornithine, and arginine.

The solid supplement composition may be in the form of powder or gel, and the solid supplement composition may comprise at least three isolated amino acid compounds selected from: aspartic acid, proline, glycine, valine, agmatine, norvaline, ornithine, and arginine.

The solid supplement composition may be in the form of powder, the amount of nitrate ion ($NO_3$—) may be at least 7 mg, and the solid supplement composition may comprise at least three isolated amino acid compounds selected from: aspartic acid, proline, glycine, valine, agmatine, norvaline, ornithine, and arginine.

The solid supplement composition may be in the form of powder or gel, and the solid supplement composition may comprise at least four isolated amino acid compounds selected from: aspartic acid, proline, glycine, valine, agmatine, norvaline, ornithine, and arginine.

The solid supplement composition may be in the form of powder, the amount of nitrate ion ($NO_3$—) may be at least 7 mg, and the solid supplement composition may comprise at least four isolated amino acid compounds selected from: aspartic acid, proline, glycine, valine, agmatine, norvaline, ornithine, and arginine.

The solid supplement composition may comprise an isolated amino acid compound that is glycine.

The composition may be in the form of powder, the amount of nitrate ion ($NO_3$—) may be at least 7 mg, and the solid supplement composition may comprise an isolated amino acid compound that is glycine.

The composition may be in the form of powder, the amount of nitrate ion ($NO_3$—) may be at least 7 mg, and the solid supplement composition may further comprise at least about 200 mg of an isolated amino acid compound that is glycine.

The solid supplement composition may further comprise an isolated amino acid compound that is aspartic acid.

The composition may be in the form of powder, the amount of nitrate ion ($NO_3$—) may be at least 7 mg, and may further comprise an isolated amino acid compound that is aspartic acid.

The composition may be in the form of powder, the amount of nitrate ion ($NO_3$—) may be at least 7 mg, may comprise beetroot, spinach, and broccoli, and may comprise isolated amino acid compounds that are aspartic acid, proline, glycine, valine, and arginine.

The foregoing and other aspects, features, and advantages will be apparent to those artisans of ordinary skill in the art from the DESCRIPTION and DRAWINGS, and from the CLAIMS.

DESCRIPTION

Overview, Terminology and Definitions

In describing implementations of an Amino Acid Compound and Composition, the following terminology will be used in accordance with the definitions and explanations set out below. Notwithstanding, other terminology, definitions, and explanations may be found throughout this document, as well.

As used herein, "Amino Acid" is a term used in its broadest sense and may refer to an Amino Acid in its many different chemical forms including a single administration Amino Acid, its physiologically active salts or esters, its combinations with its various salts, its tautomeric, polymeric and/or isomeric forms, its analog forms, its derivative forms, its products of biosynthesis, and/or its decarboxylation products. Amino Acids comprise, by way of non-limiting example: Agmatine, Beta Alanine, Arginine, Asparagine, Aspartic Acid, Carnitine, Cysteine, Glutamine, Glutamic Acid, Glycine, Histidine, L-Histidine, Leucine, Isoleucine, Lysine, Methionine, PhenylBeta Alanine, Proline, Serine, Taurine, Threonine, Tryptophan, Tyrosine, Valine, Citrulline, Creatine, Glutamine, Norvaline, Ornithine, and Phenylalanine.

Compounds containing both a carboxyl group and an amino group are typically known as Amino Acids. Amino Acids typically have the basic formula X—R, wherein X is:

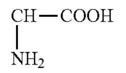

Amino Acids typically differ from one another with respect to the structure of the R group. It is the structure of the R group that typically determines the individuality and character of each Amino Acid.

For example, the R group for the Amino Acid Arginine is:

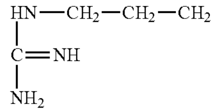

Arginine is characterized as a nonessential Amino Acid. Specifically, Arginine can be independently manufactured by the human body, and does not need to be obtained directly through dietary intake. Arginine plays a significant role in healing, cell division, immune function, the elimination of ammonia from the body and the release of hormones. Arginine is presently used in the dietary supplement industry to supplement Arginine production in the body. Arginine is also presently used in the dietary supplement industry to boost Human Growth Hormone (HGH) production, increase vasodilation, enhance blood circulation, increase oxygen flow to the muscles, and boost Nitric Oxide (NO) production. Various supplemental Arginine forms are available in the consumer marketplace.

The vasodilating effect of ingested Arginine takes considerable time to manifest since Arginine requires extensive metabolism to yield Nitric Oxide (NO). Additionally, considerable amounts of Arginine are required to produce a significant vasodilating effect, with common doses ranging from eight to twenty-four grams per day.

The R group for the Amino Acid Citrulline is:

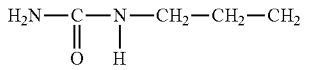

Citrulline is an alpha-Amino Acid naturally occurring in the human body, and does not need to be obtained directly through dietary intake. In vivo, Citrulline is made from the Amino Acid Ornithine, along with carbamoyl phosphate in one of the central reactions in the Urea Cycle. Citrulline is also produced during the metabolism of Arginine in the body. Citrulline is presently used in the dietary supplement industry to supplement Citrulline production in the body. By itself, Citrulline has no vasodilating properties. Citrulline is also water insoluble, which reduces its bioavailability and limits the forms in which Citrulline may be effectively used.

The R group for the Amino Acid Creatine is:

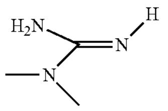

Creatine is a nonessential Amino Acid and is also a nitrogenous organic acid. Creatine is independently manufactured by the human body, and does not need to be obtained directly through dietary intake. Creatine plays a significant role in providing muscles with energy. Creatine is presently used in the dietary supplement industry to supplement Creatine production in the body. Creatine is also presently used in the dietary supplement industry to increase muscle-mass gains, improve athletic performance and strength. Creatine, by itself, has no vasodilating properties. Creatine is also water insoluble, which reduces its bioavailability and limits the forms in which Creatine may be effectively used.

The R group for the Amino Acid Glutamine is:

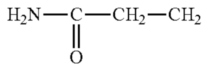

Glutamine is a nonessential Amino Acid. Glutamine is the most abundant naturally occurring, non-essential amino acid in the human body and is found circulating in the blood, as well as stored in the skeletal muscles. Glutamine plays a significant role in protein synthesis, muscle growth, and wound healing. Glutamine is presently used in the dietary supplement industry to supplement Glutamine production in the body. Glutamine is also presently used in the dietary supplement industry to maintain the body's Glutamine pool. Glutamine, by itself, has no vasodilating properties. Glutamine is also water insoluble, which reduces its bioavailability and limits the forms in which Glutamine may be effectively used. Additionally, Glutamine inhibits Nitric Acid (NO) production through downregulation of eNOS synthase.

The R group for the Amino Acid Leucine is:

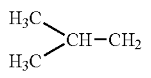

Leucine is an essential Amino Acid, meaning that Leucine is not synthesized in vivo in animals. Accordingly, Leucine must be ingested, usually as a component of proteins consumed directly through dietary intake. Leucine plays a significant role in muscle protein synthesis. Leucine can also inhibit protein degradation in skeletal muscle, as well as in the liver. Leucine is presently used in the dietary supplement industry to supplement dietary Leucine sources. Leucine is also presently used in the dietary supplement industry to promote anabolism and stimulate muscle protein synthesis. Leucine, by itself, has no vasodilating properties. Leucine is also water insoluble, which reduces its bioavailability and limits the forms in which Leucine may be effectively used.

The R group for the Amino Acid Norvaline is:

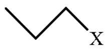

Norvaline is a nonessential Amino Acid. Specifically, Norvaline can be independently manufactured by the human body, and does not need to be obtained directly through dietary intake. Norvaline is presently used in the dietary supplement industry to supplement Norvaline production in the body. Norvaline is also presently used in the dietary supplement industry to inhibit the enzyme arginase and thus reduce the conversion of Arginine to urea. Norvaline, by itself, has no vasodilating properties, although it enhances the vasodilating properties of Arginine. Norvaline is also water insoluble, which reduces its bioavailability and limits the forms in which Leucine may be effectively used.

The R group for the Amino Acid Ornithine is:

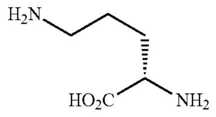

Ornithine is a non-essential Amino Acid. That is, Ornithine is independently manufactured by the human body, and does not need to be obtained directly through dietary intake. Ornithine plays a significant role in the synthesis of polyamines, specifically via the action of Ornithine decarboxylase. Ornithine is presently used in the dietary supplement industry to supplement dietary Ornithine sources. Ornithine is also presently used in the dietary supplement industry to enhance the vasodilating properties in a series of products commonly known as "NO Boosters." Ornithine exerts its vasodilating effect only by in vivo conversion to Arginine and then by following the pathway that converts Arginine to Nitric Acid (NO). Many grams of Ornithine, and a considerable amount of time, are required in order to assert its vasodilating effect.

The R group for the Amino Acid Histidine is:

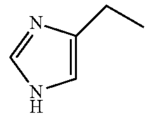

Histidine is a naturally-occurring Amino Acid and is coded for in DNA. Relatively small shifts in cellular pH will change the electrical charge of Histidine. For this reason, Histidine finds its way into considerable use as a coordinating ligand in metalloproteins, and also as a catalytic site in certain enzymes. Histidine is currently used in the dietary supplement industry to support carnosine production. Histidine, by itself, has no vasodilating properties. Additionally, Histidine is very poorly water soluble, a fact that limits its bioavailability and utility. Histidine is presently used in the dietary supplement industry in the forms of single administration Histidine and Histidine HCl.

The R group for the Amino Acid Beta Alanine is:

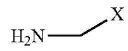

Beta Alanine is the only naturally-occurring Beta Amino Acid. A Beta Amino Acid is one in which the Amino group is located at the beta position (i.e. two atoms away) from the Carboxyl group. Beta Alanine is formed in vivo through the degradation of dihydrouracil and carnosine. Beta Alanine is the rate-limiting precursor of carnosine. Therefore, carnosine levels are limited by the amount of available Beta Alanine. Beta Alanine, by itself, has no vasodilating properties. Additionally, Beat Alanine is somewhat water soluble, which limits its bioavailability and utility. Beta Alanine is presently used in the dietary supplement industry to support carnosine production.

The chemical structure of Agmatine is:

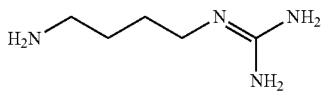

Agmatine is the decarboxylation product of the Amino Acid Arginine and is an intermediate in polyamine biosynthesis. Agmatine is synthesized in the brain and stored in synaptic vesicles in regionally selective neurons. Agmatine is released by depolarization and is inactivated by agmatinase. Agmatine binds to alpha2-adrenoceptors and imidazoline binding sites. Agmatine likewise blocks N-methyl-D-aspartic acid (NMDA) receptor channels and other ligand-gated cationic channels. Additionally, agmatine inhibits nitric oxide synthase, and induces the release of some peptide hormones. Agmatine modulates nitric oxide through various mechanisms. Agmatine stimulates some types of nitric oxide synthase (NOS) while inhibiting others. Agmatine inhibits Nitric Oxide production by inhibiting NOS. Agmatine is presently used in the dietary supplement industry in the forms of single administration Agmatine and Agmatine Sulfate.

Carnitine is a quaternary ammonium compound biosynthesized from the amino acids lysine and methionine. Acetyl-L-Carnitine is an alternative form of carnitine with an acetyl group coupled with the hydroxyl group of the third carbon molecule. Propionyl-L-carnitine is another alternative form of carnitine that contains a propionyl group coupled with the third carbon molecule. The chemical structures of Carnitine, Acetyl-L-Carnitine, and Propionyl-L-carnitine are as follows:

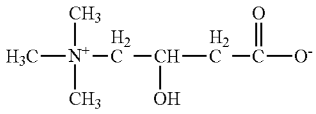

L-Carnitine

-continued

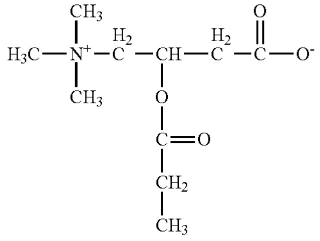

Propionyl-L-Carnitine

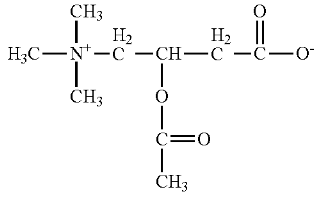

Acetyl-L-Carnitine

Significantly, neither carnitine nor its alternative forms possess vasodilating properties. In addition, since carnitine and its alternative forms are bipolar molecules, their solubility might be lowered with respect to pH. Carnitine is presently used in the dietary supplement industry to supplement Carnitine production in the body. Carnitine is also presently used in the dietary supplement industry to improve athletic performance, enhance mood, and boost immune response. Various supplemental Carnitine forms are available in the consumer marketplace.

Taurine is a derivative of the sulfur-containing amino acid Cysteine:

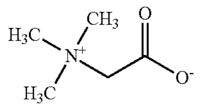

Taurine by itself has no vasodilating properties. Taurine is presently used in the dietary supplement industry to supplement Taurine production in the body. Taurine is also presently used in the dietary supplement industry to improve athletic performance and resist muscle cramps. Various supplemental Taurine forms are available in the consumer marketplace, including many sports supplements and energy drinks.

As used herein, “Composition” is a term used in its broadest sense and may refer to a mixture of constituent substances or ingredients. “Mixture” is a term used in its broadest sense and may refer to two or more constituent substances or ingredients (chemical species present in a system) which have been combined (not necessarily in fixed proportions and not necessarily with chemical bonding and not necessarily so that each substance retains its own chemical identity). Mixtures can be the product of a blending or mixing of chemical substances like elements and compounds, without chemical bonding or other chemical change, so that each ingredient substance retains its own chemical properties and makeup. Mixtures can be either homogeneous or heterogeneous. A homogeneous mixture is a type of mixture in which the composition is uniform. A heterogeneous mixture is a type of mixture in which the composition can easily be identified, as there are two or more phases present. A homogeneous mixture in which there is both a solute and solvent present is also a solution.

A "Compound" is a term used in its broadest sense and may refer to a chemical substance comprising two or more different chemically bonded chemical constituent elements or ingredients, with a fixed ratio or proportion by weight. The atoms within a compound can be held together by a variety of interactions, ranging from covalent bonds to electrostatic forces in ionic bonds. The physical and chemical properties of compounds are different from those of their constituent elements. This is one of the main criteria for distinguishing a compound from a mixture of elements or other substances because a mixture's properties are generally closely related to and dependent on the properties of its constituents. However, some mixtures are so intimately combined that they have some properties similar to compounds. Another criterion for distinguishing a compound from a mixture is that the constituents of a mixture can usually be separated by simple, mechanical means such as filtering, evaporation, or use of a magnetic force, but the components of a compound can only be separated by a chemical reaction. Conversely, mixtures can be created by mechanical means alone, but a compound can only be created (either from elements or from other compounds, or a combination of the two) by a chemical reaction.

Thus, for purposes of this disclosure, "Composition" may refer to a mixture of at least one Amino Acid in combination with at least a Nitrate, a Nitrite, or both from any source.

As used herein, "Nitrate" is a term used in its broadest sense and may refer to an Nitrate in its many different chemical forms including a salt of Nitric Acid, a single administration Nitrate, its physiologically active salts, its combinations with its various salts, its tautomeric, polymeric and/or isomeric forms, its analog forms, and/or its derivative forms. Nitrate comprises, by way of non-limiting example, many different chemical forms including dinitrate and trinitrate. Nitrates may be salts, or mixed salts, of Nitric Acid (HNO3) and comprise one Nitrogen atom and three Oxygen atoms (NO3). For the exemplary purposes of this disclosure, Nitrate may comprise salts of Nitrate such as sodium nitrate, potassium nitrate, calcium nitrate, and the like. For the exemplary purposes of this disclosure, Nitrate may include mixed salts of Nitrate such as nitrate orotate, and the like. Furthermore, for the exemplary purposes of this disclosure, other appropriate sources of nitrates may be juice, extract, powder and the like of Cabbage, Spinach, Beetroot, Artichoke, Asparagus, Broad Bean, Eggplant, Garlic, Onion, Green Bean, Mushroom, Pea, Pepper, Potato, Summer Squash, Sweet Potato, Tomato, Watermelon, Broccoli, Carrot, Cauliflower, Cucumber, Pumpkin, Chicory, Dill, Turnip, Savoy Cabbage, Celeriac, Chinese Cabbage, Endive, Fennel, Kohlrabi, Leek, Parsley, Celery, Cress, Chervil, Lettuce, Rocket (Rucola), and the like.

As used herein, "Nitrite" is a term used in its broadest sense and may refer to an Nitrite in its many different chemical forms including a salt of Nitrous Acid, a single administration Nitrite, its physiologically active salts, its combinations with its various salts, its tautomeric, polymeric and/or isomeric forms, its analog forms, and its derivative forms. Nitrite comprises, by way of non-limiting example, many different chemical forms including dinitrite and trinitrite. Nitrites may be salts, or mixed salts, of Nitrous Acid (HNO2) and comprise one Nitrogen atom and two Oxygen atoms (NO2). For the exemplary purposes of this disclosure, Nitrite may comprise salts of Nitrite such as sodium nitrite, potassium nitrite, calcium nitrite, and the like. For the exemplary purposes of this disclosure, Nitrite may comprise mixed salts of Nitrite such as nitrite orotate, and the like. Furthermore, for the exemplary purposes of this disclosure, other appropriate sources of Nitrites may be juice, extract, powder and the like of Cabbage, Spinach, Beetroot, Artichoke, Asparagus, Broad Bean, Eggplant, Garlic, Onion, Green Bean, Mushroom, Pea, Pepper, Potato, Summer Squash, Sweet Potato, Tomato, Watermelon, Broccoli, Carrot, Cauliflower, Cucumber, Pumpkin, Chicory, Dill, Turnip, Savoy Cabbage, Celeriac, Chinese Cabbage, Endive, Fennel, Kohlrabi, Leek, Parsley, Celery, Cress, Chervil, Lettuce, Rocket (Rucola), and the like.

Nitrates and Nitrites are commercially available in various preparations, including natural preparations, and are used in various applications. In the case of ingestion by humans, Nitrate ($NO_3$) is typically reduced to Nitrite ($NO_2$) in the epithelial cells of blood vessels. In vivo, Nitrite ($NO_2$) reacts with a thiol donor, principally glutathione, to yield Nitric Oxide (NO).

As used herein, "acceptable additive" or "additive" are terms used in their broadest sense. Particular implementations of the compositions described in this document may also comprise an additive (e.g. one of a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, a thickener, and combinations thereof) and/or a carrier (e.g. one of an excipient, a lubricant, a binder, a disintegrator, a diluent, an extender, a solvent, a suspending agent, a dissolution aid, an isotonization agent, a buffering agent, a soothing agent, an amphipathic lipid delivery system, and combinations thereof). These additives may be solids or liquids, and the type of additive may be generally chosen based on the type of administration being used. Those of ordinary skill in the art will be able to readily select suitable pharmaceutically effective additives from the disclosure in this document. In particular implementations, acceptable additives may include, by non-limiting example, calcium phosphate, cellulose, stearic acid, croscarmelose cellulose, magnesium stearate, and silicon dioxide.

As used in this document, "effective" is a phrase used in its broadest sense, including, by non-limiting example, effective in a clinical trial, for a specific patient, or only placebo-effective.

As used in this document, "acceptable" is a phrase used in its broadest sense and may describe ingredients of a composition that meet Food and Drug Administration (FDA) standards, United States Pharmacopeial Standards (USP), US Department of Agriculture (USDA) standards for food-grade materials, commonly accepted standards of the nutritional supplement industry, industry standards, botanical standards, or standards established by any individual. These standards may delineate acceptable ranges of aspects of ingredients of a composition such as edibility, toxicity, pharmacological effect, or any other aspect of a chemical, composition, or preparation used in implementations of a composition.

Components/Compounds/Compositions

A first implementation is an Arginine compound of the formula:

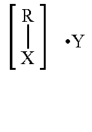

wherein;

R is the Arginine group identified and defined above;

X is the Amino Acid base identified and defined above; and

Y is selected from the group consisting of a Nitrate and a Nitrite.

Applicants have cost-effectively synthesized Arginine Nitrate by combining nitric acid and Arginine, mixing with water or another polar, easily evaporated solvent like methanol, alcohol, pyridine, and the like, and leaving to crystallize. Further nitratization can take place, yielding Arginine Dinitrate or Arginine Trinitrate. An alternative implementation may comprise using Nitrous Acid ($HNO_2$) instead of Nitric Acid ($HNO_3$), thus yielding Arginine Nitrite. Arginine Nitrite has the same effects as Arginine Nitrate, the only difference being that it requires one less step to yield Nitric Oxide (NO—). Mixed salts may also be used, such as in the non-limiting example of Arginine Nitrate-Orotate.

A second implementation is a Citrulline compound of the formula:

wherein;

R is the Citrulline group identified and defined above;

X is the Amino Acid base identified and defined above; and

Y is selected from the group consisting of a Nitrate and a Nitrite.

Applicants have cost-effectively synthesized Citrulline Nitrate by combining nitric acid and Citrulline, mixing with water or another polar, easily evaporated solvent like methanol, alcohol, pyridine, and the like, and leaving to crystallize. Further nitratization can take place, yielding Citrulline Dinitrate or Citrulline Trinitrate. An alternative implementation may comprise using Nitrous Acid ($HNO_2$) instead of Nitric Acid ($HNO_3$), thus yielding Citrulline Nitrite. Citrulline Nitrite has the same effects as Citrulline Nitrate, the only difference being that it requires one less step to yield Nitric Oxide (NO—). Mixed salts may also be used, such as in the non-limiting example of Citrulline Nitrate-Orotate.

A third implementation is a Creatine compound of the formula:

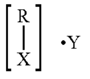

wherein;

R is the Creatine group identified and defined above;

X is the Amino Acid base identified and defined above; and

Y is selected from the group consisting of a Nitrate and a Nitrite.

Applicants have cost-effectively synthesized Creatine Nitrate by combining nitric acid and Creatine, mixing with water or another polar, easily evaporated solvent like methanol, alcohol, pyridine, and the like, and leaving to crystallize. Further nitratization can take place, yielding Creatine Dinitrate or Creatine Trinitrate. An alternative implementation may comprise using Nitrous Acid ($HNO_2$) instead of Nitric Acid ($HNO_3$), thus yielding Creatine Nitrite. Creatine Nitrite has the same effects as Creatine Nitrate, the only difference being that it requires one less step to yield Nitric Oxide (NO—). Mixed salts may also be used, such as in the non-limiting example of Creatine Nitrate-Orotate.

A fourth implementation is a Glutamine compound of the formula:

wherein;

R is the Glutamine group identified and defined above;

X is the Amino Acid base identified and defined above; and

Y is selected from the group consisting of a Nitrate and a Nitrite.

Applicants have cost-effectively synthesized Glutamine Nitrate by combining nitric acid and Glutamine, mixing with water or another polar, easily evaporated solvent like methanol, alcohol, pyridine, and the like, and leaving to crystallize. Further nitratization can take place, yielding Glutamine Dinitrate or Glutamine Trinitrate. An alternative implementation comprises using Nitrous Acid ($HNO_2$) instead of Nitric Acid ($HNO_3$), thus yielding Glutamine Nitrite. Glutamine Nitrite has the same effects as Glutamine Nitrate, the only difference being that it requires one less step to yield Nitric Oxide (NO—). Mixed salts may also be used, such as in the non-limiting example of Glutamine Nitrate-Orotate.

A fifth implementation is a Leucine compound of the formula:

wherein;

R is the Leucine group identified and defined above;

X is the Amino Acid base identified and defined above; and

Y is selected from the group consisting of a Nitrate and a Nitrite.

Applicants have cost-effectively synthesized Leucine Nitrate by combining nitric acid and Leucine, mixing with water or another polar, easily evaporated solvent like methanol, alcohol, pyridine, and the like, and leaving to crystallize. Further nitratization can take place, yielding Leucine Dinitrate or Leucine Trinitrate. An alternative implementation comprises substituting the Amino Acids Valine or Isoleucine for Leucine. Another alternative implementation comprises substituting Nitrous Acid ($HNO_2$) for Nitric Acid ($HNO_3$), thus yielding Leucine Nitrite. Leucine Nitrite has the same effects as Leucine Nitrate, the only difference being that it requires one less step to yield Nitric Oxide (NO—). Mixed salts may also be used, such as in the non-limiting example of Leucine Nitrate-Orotate.

A sixth implementation is a Norvaline compound of the formula:

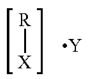

wherein;

R is the Norvaline group identified and defined above;

X is the Amino Acid base identified and defined above; and

Y is selected from the group consisting of a Nitrate and a Nitrite.

Applicants have cost-effectively synthesized Norvaline Nitrate by combining nitric acid and Norvaline, mixing with water or another polar, easily evaporated solvent like methanol, alcohol, pyridine, and the like, and leaving to crystallize. Further nitratization can take place, yielding Norvaline Dinitrate or Norvaline Trinitrate. An alternative implementation comprises substituting Nitrous Acid ($HNO_2$) for Nitric Acid ($HNO_3$), thus yielding Norvaline Nitrite. Norvaline Nitrite has the same effects as Norvaline Nitrate, the only difference being that it requires one less step to yield Nitric Oxide (NO—). Mixed salts may also be used, such as in the non-limiting example of Norvaline Nitrate-Orotate.

A seventh implementation is an Ornithine compound of the formula:

wherein;

R is the Ornithine group identified and defined above;

X is the Amino Acid base identified and defined above; and

Y is selected from the group consisting of a Nitrate and a Nitrite.

Applicants have cost-effectively synthesized Ornithine Nitrate by combining nitric acid and Ornithine, mixing with water or another polar, easily evaporated solvent like methanol, alcohol, pyridine, and the like, and leaving to crystallize. Further nitratization can take place, yielding Ornithine Dinitrate or Ornithine Trinitrate. An alternative implementation comprises using Nitrous Acid ($HNO_2$) instead of Nitric Acid ($HNO_3$), thus yielding Ornithine Nitrite. Ornithine Nitrite has the same effects as Ornithine Nitrate, the only difference being that it requires one less step to yield Nitric Oxide (NO—). Mixed salts may also be used, such as in the non-limiting example of Ornithine Nitrate-Orotate.

An eighth implementation is a Histidine compound of the formula:

wherein;

R is the Histidine group identified and defined above;

X is the Amino Acid base identified and defined above; and

Y is selected from the group consisting of a Nitrate and a Nitrite.

Applicants have cost-effectively synthesized Histidine Nitrate by combining nitric acid and Histidine, mixing with water or another polar, easily evaporated solvent like methanol, alcohol, pyridine, and the like, and leaving to crystallize. Further nitratization can take place, yielding Histidine Dinitrate or Histidine Trinitrate. An alternative implementation comprises using Nitrous Acid ($HNO_2$) instead of Nitric Acid ($HNO_3$), thus yielding Histidine Nitrite. Histidine Nitrite has the same effects as Histidine Nitrate, the only difference being that it requires one less step to yield Nitric Oxide (NO—). Mixed salts may also be used, such as in the non-limiting example of Histidine Nitrate-Orotate.

A ninth implementation is a Beta Alanine compound of the formula:

wherein;

R is the Beta Alanine group identified and defined above;

X is the Amino Acid base identified and defined above; and

Y is selected from the group consisting of a Nitrate and a Nitrite.

Applicants have cost-effectively synthesized Beta Alanine Nitrate by combining nitric acid and Beta Alanine, mixing with water or another polar, easily evaporated solvent like methanol, alcohol, pyridine, and the like, and leaving to crystallize. Further nitratization can take place, yielding Beta Alanine Dinitrate or Beta Alanine Trinitrate. An alternative implementation comprises using Nitrous Acid ($HNO_2$) instead of Nitric Acid ($HNO_3$), thus yielding Beta Alanine Nitrite. Beta Alanine Nitrite has the same effects as Beta Alanine Nitrate, the only difference being that it requires one less step to yield Nitric Oxide (NO—). Mixed salts may also be used, such as in the non-limiting example of Beta Alanine Nitrate-Orotate.

A tenth implementation is an Agmatine compound of the formula:

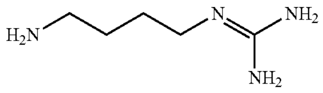

wherein;

n the group consisting of a Nitrate and a Nitrite.

•Y cants have cost-effectively synthesized Agmatine Nitrate by combining nitric acid and Agmatine, mixing with water or another polar, easily evaporated solvent like methanol, alcohol, pyridine, and the like, and leaving to crystallize. Further nitratization can take place, yielding Agmatine Dinitrate or Agmatine Trinitrate. An alternative implementation comprises using Nitrous Acid ($HNO_2$) instead of Nitric Acid ($HNO_3$), thus yielding Agmatine Nitrite. Agmatine Nitrite has the same effects as Agmatine Nitrate, the only difference being that it requires one less step to yield Nitric Oxide (NO—). Mixed salts may also be used, such as in the non-limiting example of Agmatine Nitrate-Orotate.

Other implementations involve compositions instead of compounds. Using an independent source of nitrates and/or nitrites that is mixed with any of the amino acids disclosed in this document to form a composition can obtain substantially the same effects as the amino acid nitrate or nitrite compounds discussed in this document.

Such an amino acid composition might be depicted by the formula X—R+Y. "X—R" represents an amino acid as discussed previously and "Y" represents a Nitrate and/or Nitrite. But instead of forming a compound, they are mixed together (represented by the "+") to form a composition.

For the exemplary purposes of this disclosure, following is a variety of specific examples of amino acid compositions.

Composition 1: Creatine Nitrate 100-1000 mg in capsules. Dosage is 3 capsules twice daily.

Composition 2 (Powder Form): Serving Size: 4 grams. Creatine Nitrate 3-3.5 grams. Vitamin C 500-1000 mg.

Composition 3 (Sports Drink): 0.5-3 Grams Arginine Nitrate. 0.5-2 Grams Taurine. 1-3 grams Sugar or appropriate Sweetener. Artificial Coloring. Purified Water till 500 ml of total Volume.

Composition 4 (sublingual tablets; amounts are per tablet): Agmatine Nitrate 10-100 mg. Maltulose 200 mg. Artificial Cherry Flavor. Melt Maltulose, add in slowly the Agmatine Nitrate and the flavor, and pour in the tablet machine.

Composition 5 (Tablets Containing Arginine and Potassium Nitrate for Blood Pressure support). Per tablet: Arginine 250-700 mg. Potassium Nitrate 50-500 mg. Corn Starch till the desired volume for the tablet machine is obtained.

Composition 6 (for healthy blood pressure support): 500-1000 mg Arginine (As arginine nitrate)+250-500 mg Celery Seed Extract+100-300 mg Dried Garlic Powder in airseal Capsules.

Composition 7 (For improved Sexual Performance): 500-1000 mg grams Agmatine+1-2 grams D-aspartic Acid (as D-Aspartic Acid Nitrate)+1-2 grams dried onion powder (onion also increases testosterone) in capsules.

Composition 8 (Improved Strength): Creatine (As Creatine Malate) 2-3 grams and Calcium Nitrate 500 mg.

Composition 9 (Improved Muscle Endurance Sports Drink): Beta Alanine 1-2 grams+Citrulline (As Citrulline Nitrate) 250-500 mg+Potassium Nitrate 100-200 mg+Sodium Nitrate 50-100 mg+Magnesium Nitrate 200 mg Artificial COlouring Sweetener and flavour Purified Water till 500 ml.

Composition 10 (Improved Muscle anabolism and recovery): Leucine 1-5 grams Isoleucine 1-2 grams Valine 1-2 grams Spinach Extract (Standarized for nitrate content and ecdysterone content minimum 1% and 10% respectively) 5 grams.

Composition 11 (Improved Mental Performance): 500-1000 mg Tyrosine+250-500 mg Phenylalanine (as Phenylalanine Nitrate)+1000-2000 mg Glycine+200-300 mg Lithium Nitrate+300-600 mg Hystidine In Time Release Tablets.

Composition 12 (Growth Hormone Support): Arginine 2-4 grams+Ornithine 1-2 grams+Magnesium Nitrate 500 mg.

Composition 13 (Hair Growth Support As External Use Cream): Lysine Nitrite 1 gram Hydroxyproline Nitrate 5 grams Methionine nitrate 5 grams Euserine Cream Base 100 grams.

Composition 14 (Immune Support effervescent tabs): Glutamine 400-800 mg Hystidine (As histidine nitrate) 250-500 mg Cysteine (As N-Acetyl Cysteine) 200-300 mg PArsley Powder (Standarized for Vitamin C and nitrate) 125-250 mg.

Administration and Dosage Forms

Compounds, Compositions and/or formulations may be administered in any form, including one of a capsule, a cachet, a pill, a tablet, a powder, a granule, a pellet, a bead, a particle, a troche, a lozenge, a pastille, a solution, an elixir, a syrup, a tincture, a suspension, an emulsion, a mouthwash, a spray, a drop, an ointment, a cream, a gel, a paste, a transdermal patch, a suppository, a pessary, cream, a foam, and combinations thereof for example.

Implementations of Amino Acid Compounds and Compositions may conveniently be presented in unit dosage form. Unit dosage formulations may be those containing a daily dose or unit, a daily sub-dose, or an appropriate fraction thereof, of the administered components as described herein.

A dosage unit may include an Amino Acid Compound or Composition. In addition, a dosage unit may include an Amino Acid Compound or Composition admixed with a pharmaceutically acceptable additive(s), and/or any combination thereof.

The dosage units may be in a form suitable for administration by standard routes. In general, the dosage units may be administered, by non-limiting example, by the topical (including buccal and sublingual), transdermal, oral, rectal, ophthalmic (including intravitreal or intracameral), nasal, vaginal, and/or parenteral (including subcutaneous, intramuscular, intravenous, intradermal, intratracheal, and epidural) routes and many other delivery methods and/or systems known to those of ordinary skill in the art. Implementations of an Amino Acid Compound or Composition may also be administered through use of amphipathic lipid delivery systems (such as liposomes and unilamellar vesicles). Those of ordinary skill in the art will readily be able to select additional pharmaceutically acceptable additives to enable delivery of implementations of a pharmaceutical composition from the disclosure in this document.

For the exemplary purposes of this disclosure, oral delivery may be a particularly advantageous delivery route for administration to humans and animals of implementations of a pharmaceutical composition, optionally formulated with appropriate pharmaceutically acceptable additives to facilitate administration.

Manufacture

Implementations of Amino Acid Nitrate and/or Nitrite Compounds or Compositions may be synthesized or created in a wide variety of manners, and may be made from a wide variety of materials. Those of ordinary skill in the art will readily be able to select appropriate materials and methods to manufacture and use the compounds and compositions disclosed herein.

Accordingly, although there are a variety of method implementations for producing pharmaceutical compositions, for the exemplary purposes of this disclosure, a method implementation for producing an Amino Acid Compound may comprise: measuring specific quantities of Amino Acid, Nitric or Nitrous Acid and water or any other polar, easily evaporated solvent such as methanol, alcohol, pyridine, and the like mixed in a specific order the measured quantities of Amino Acid, Nitric or Nitrous Acid and water or solvent, and any additional pharmaceutically acceptable additives or inert ingredients, and then separating the pharmaceutical composition into discrete quantities for distribution and/or administration.

Measuring specific quantities of Amino Acid, Nitric or Nitrous Acid and water or solvent, and pharmaceutically acceptable additives or inert ingredients, may involve any number of steps and implementing components, and measuring specific quantities of Amino Acid, Nitric or Nitrous Acid and water or solvent, and pharmaceutically acceptable additives or inert ingredients, may be accomplished readily from this disclosure. For the exemplary purposes of this disclosure, measuring specific quantities of Amino Acid, Nitric or Nitrous Acid and water or solvent, and pharmaceutically acceptable additives or inert ingredients, may comprise using a scale, a solid or liquid dispensing apparatus, or other measurement device capable of measuring solid mass or liquid volume to produce a desired quantity of Amino Acid, Nitric or Nitrous Acid and water or solvent, and pharmaceutically acceptable ingredient.

It should be appreciated that any of the components of particular implementations of an Amino Acid Compound or Composition may be used as supplied commercially, or may be preprocessed by, by non-limiting example, any of the methods and techniques of agglomeration, air suspension chilling, air suspension drying, balling, coacervation, comminution, compression, pelletization, cryopelletization, extrusion, granulation, homogenization, inclusion Compoundation, lyophilization, melting, mixed, molding, pan coating, solvent dehydration, sonication, spheronization, spray chilling, spray congealing, spray drying, or other processes known in the art depending in part on the dosage form desired. The various components may also be pre-coated or encapsulated as known in the art. It will also be clear to one of ordinary skill in the art that appropriate additives may also be introduced to the composition or during the processes to facilitate the preparation of the dosage forms, depending on the need of the individual process.

Mixing the measured quantities of Amino Acid, Nitric or Nitrous Acid and water or solvent, and pharmaceutically acceptable additives or inert ingredients for Compounds, or mixing the measured quantities of Amino Acid, Nitrate and/or Nitrite sources, and pharmaceutically acceptable additives or inert ingredients for Compositions, may involve any number of steps and implementing components, and may be accomplished readily from this disclosure.

For the exemplary purposes of this disclosure, mixing the measured quantities of Amino Acid, Nitric or Nitrous Acid and water or solvent, and pharmaceutically acceptable additives or inert ingredients, may comprise combining the measured quantities of m Amino Acid, Nitric or Nitrous Acid and water or solvent, and pharmaceutically acceptable additives or inert ingredients, under the influence of physical, ultrasonic, or electrostatic forces to create a desired degree of intermingling and/or chemical reaction of the Amino Acid, Nitric or Nitrous Acid and water or solvent and any pharmaceutically acceptable ingredients. The mixed may be accomplished when the Amino Acid, Nitric or Nitrous Acid and water or solvent and/or any pharmaceutically acceptable ingredients are in a solid, liquid, or semi-solid state.

Separating the Amino Acid Compound or Composition into discrete quantities for distribution may involve any number of steps and implementing components, and separating the Amino Acid Compound or Composition into discrete quantities for distribution may be accomplished readily from this disclosure. For the exemplary purposes of this disclosure, separating the Amino Acid Compound or Composition into discrete quantities for distribution may involve utilizing a specific piece of equipment, for example, a conventional tablet forming apparatus to shape the formed composition into individual tablets, each containing a desired dose of Amino Acid Compound or Composition. The separating process may be accomplished when the Amino Acid Compound or Composition is in a solid, liquid, or semisolid state.

Those of ordinary skill in the art will be able to readily select manufacturing equipment and pharmaceutically acceptable additives or inert ingredients to manufacture implementations of an Amino Acid Compound or Composition. For the exemplary purposes of this disclosure, some examples of pharmaceutically acceptable additives or inert ingredients and manufacturing process are included below, particularly those that relate to manufacture of implementations of an Amino Acid Compound or Composition in tablet form. Notwithstanding the specific examples given, it will be understood that those of ordinary skill in the art will readily appreciate how to manufacture implementations of an Amino Acid Compound or Composition according to the other methods of administration and delivery disclosed in this document.

Accordingly, compounds and Compositions may include a acceptable additive (e.g. one of a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, a thickener, and combinations thereof) and/or a acceptable carrier (e.g. one of an excipient, a lubricant, a binder, a disintegrator, a diluent, an extender, a solvent, a suspending agent, a dissolution aid, an isotonization agent, a buffering agent, a soothing agent, an amphipathic lipid delivery system, and combinations thereof).

For example, a particular implementation of an Amino Acid Compound or Composition may include a lubricant. Lubricants are any anti-sticking agents, glidants, flow promoters, and the like materials that perform a number of functions in tablet manufacture, for example, such as improving the rate of flow of the tablet granulation, preventing adhesion of the tablet material to the surface of the dies and punches, reducing interparticle friction, and facilitating the ejection of the tablets from the die cavity. Lubricants may comprise, for example, magnesium stearate, calcium stearate, talc, and colloidal silica.

Particular implementations of an Amino Acid Compound or Composition may also include a binder. Binders are any agents used to impart cohesive qualities to powdered material through particle-particle bonding. Binders may include, for example, matrix binders (e.g. dry starch, dry sugars), film binders (e.g. celluloses, bentonite, sucrose), and chemical binders (e.g. polymeric cellulose derivatives, such as methyl cellulose, carboxy methyl cellulose, and hydroxy propyl cellulose); and other sugar, gelatin, non-cellulosic binders and the like.

Disintegrators may be used in particular implementations of an Amino Acid Compound or Composition to facilitate the breakup or disintegration of tablets after administration. Disintegrators may include, for example, starch, starch derivatives, clays (e.g. bentonite), algins, gums (e.g. guar gum), cellulose, cellulose derivatives (e.g. methyl cellulose, carboxymethyl cellulose), croscarmellose sodium, croscarmellose cellulose, and other organic and inorganic materials.

Implementations of an Amino Acid Compound or Composition may include diluents, or any inert substances added to increase the bulk of the Amino Acid Compound to make a tablet a practical size for compression. Diluents may include, for example, calcium phosphate, calcium sulfate, lactose, mannitol, magnesium stearate, potassium chloride, and citric acid, among other organic and inorganic materials.

Buffering agents may be included in an Amino Acid Compound or Composition and may be any one of an acid and a base, where the acid is, for example, propionic acid, p-toluenesulfonic acid, salicylic acid, stearic acid, succinic acid, tannic acid, tartaric acid, thioglycolic acid, or toluenesulfonic acid, and the base is, for example, ammonium hydroxide, potassium hydroxide, sodium hydroxide, sodium hydrogen carbonate, aluminum hydroxide, calcium carbonate, and other organic and inorganic chemicals.

With respect to delivery of particular implementations of an Amino Acid Compound or Composition, for the exemplary purposes of this disclosure, tablets may be utilized. Tablets are any solid pharmaceutical dosage form containing a pharmaceutically acceptable active agent or agents to be administered with or without suitable pharmaceutically acceptable additives and prepared either by compression or molding methods well known in the art. Tablets have been in widespread use and remain popular as a dosage form because of the advantages afforded both to the manufacturer (e.g., simplicity and economy of preparation, stability, and convenience in packaging, shipping, and dispensing) and the patient (e.g., accuracy of dosage, compactness, portability, blandness of taste, and ease of administration). Although tablets are most frequently discoid in shape, they may also be round, oval, oblong, cylindrical, rectangular or triangular, for example. The tablets may be optionally scored so that they may be separated into different dosages. They may differ greatly in size and weight depending on the amount of the pharmaceutically acceptable active agent or agents present and the intended route of administration. They are divided into two general classes, (1) compressed tablets, and (2) molded tablets.

Tablets and other orally discrete dosage forms, such as capsules, cachets, pills, granules, pellets, beads, and particles, for example, may optionally be coated with one or more enteric coatings, seal coatings, film coatings, barrier coatings, compress coatings, fast disintegrating coatings, or enzyme degradable coatings for example. Multiple coatings may be applied for desired performance. Further, dosage forms may be designed for, by non-limiting example, immediate release, pulsatile release, controlled release, extended release, delayed release, targeted release, synchronized release, or targeted delayed release. For release/absorption control, carriers may be made of various component types and levels or thicknesses of coats. Such diverse carriers may be blended in a dosage form to achieve a desired performance. In addition, the dosage form release profile may be effected by a polymeric matrix composition, a coated matrix composition, a multi-particulate composition, a coated multi-particulate composition, an ion-exchange resin-based composition, an osmosis-based composition, or a biodegradable polymeric composition.

While manufacture of implementations of an Amino Acid Compound and Composition have been described in particular sequences of steps and/or in particular forms, it will be understood that such manufacture is not limited to the specific order of steps or forms as disclosed. Any steps or sequences of steps of manufacture of implementations of an Amino Acid Compound and Composition in any form are given as examples of possible steps or sequences of steps or potential forms and not as limitations, since many possible manufacturing processes and sequences of steps may be used to manufacture Amino Acid Compound and Composition implementations in a wide variety of forms.

Use

Implementations of an Amino Acid Compound or Composition are particularly useful in increasing bioabsorption and vasodilation in humans and animals. However, implementations are not limited to uses relating to bioabsorption or vasodilation modification, and the like. Rather, any description relating to the foregoing is for the exemplary purposes of this disclosure. It will be understood that implementations of an Amino Acid Compound or Composition may encompass a variety of uses and are not limited in their uses. For example, possible uses may be, by non-limiting example, prevention of Nitrate tolerance, enhanced water solubility, increased distribution to muscles, increased athletic performance, and/or countering Nitric Oxide inhibiting effects of certain Amino Acids.

In conventional preparations of Nitrate compounds, "tolerance," a particular side effect, has been observed in many patients. This is unfortunate because the effectiveness of Nitrate on vasodilation is well documented. "Tolerance" occurs when a subject's reaction to Nitrate decreases so that larger doses are required to achieve the same effect. A Mar. 3, 2000 report in the British Journal of Pharmacology indicates that "tolerance to the dilator effects of nitrates remains a persisting therapeutic problem." Raymond J. MacAllister "Arginine and Nitrate Tolerance" available at http://www.nature.com/bjp/journal/v130/n2/full/0703340a.html, the contents of which are hereby incorporated herein by reference.

Empirical studies indicate that Nitrates are useful for their vasolidating effects. Common Nitrates include nitroglycerin and isosorbide dinitrate. Nitrates exert their vasodilating effect through their reduction to Nitrites. In vivo, Nitrates are reduced to Nitrites and, in the blood vessels' epithelial cells, Nitrite reacts with a thiol donor (mainly glutathione) to yield Nitric Oxide. Louis J. Ignarro, "After 130 years, the Molecular Mechanism of Action of Nitroglycerin is Revealed" (Jun. 11, 2002) available at http://www.pnas.org/cgi/content/full/99/12/7816?ck=nck, the contents of which are hereby incorporated herein by reference.

The Nitric Oxide inhibiting characteristics of the Amino Acid Glutamine have been well documented in a number of studies. In particular, a Mar. 28, 2006 report in the American Journal of Physiology has found that Glutamine inhibits Nitric Oxide production by downregulation of eNOS synthase. Masao Kakoki, et al. "Amino acids as Modulators of Endothelium-Derived Nitric Oxide." available at http://ajprenal.physiology.org/cgi/content/full/291/2/F297, the contents of which are hereby incorporated by reference.

A January 2006 *Journal of Nutrition* report indicates that the Amino Acid Leucine promotes anabolism and stimulates muscle protein synthesis. Michael J. Rennie, et al. "Branched-Chain Amino Acids as Fuels and Anabolic Signals in Human Muscle" available at http://jn.nutrition.org/cgi/content/full/136/1/264S, the contents of which are hereby incorporated by reference.

Empirical studies indicate that the Amino Acid Norvaline inhibits the enzyme arginase and thus decreases the rate of conversion of the Amino Acid Arginine to urea. Takeyori Saheki, et al. "Regulation of Urea Synthesis in Rat Liver" available at http://jb.oxfordjournals.org/cgi/content/abstract/86/3/745?ijkey=5d134456b7443ca36c80926946 2276e532549798&keytype2=tf_ipsecsha, the contents of which are hereby incorporated by reference.

An October 2004 *Journal of Nutrition* report indicates that the Amino Acid Ornithine promotes anabolism and stimulates muscle protein synthesis. Michael J. Rennie, et al. "Branched-Chain Amino Acids as Fuels and Anabolic Signals in Human Muscle" available at http://jn.nutrition.org/cgi/content/full/136/1/264S, the contents of which are hereby incorporated by reference.

Empirical studies indicate that the Amino Acids Beta-Beta Alanine and L-Histidine support carnosine production. M. Dunnett, "Influence of Oral Beta-Beta Alanine and L-Histidine Supplementation on the Carnosine Content of the Gluteus Medius" Equine Veterinary Journal Supplement, available at http://www.ncbi.nlm.nih.gov/sites/entrez?Db=pubmed&Cmd=ShowDetailView&TermToSearch=

10659307&ordinalpos=4&itool=EntrezSystem2.PEntrez.Pubmed.Pubmed, the contents of which are hereby incorporated by reference.

Empirical studies further indicate that the Amino Acids Beta Alanine and L-Histidine increase muscle power, recuperation and stamina. Yoshihiro Suzuki "High Level of Skeletal Muscle Carnosine Contributes to the Latter Half of Exercise Performance During 30-S Maximal Cycle Ergometer Sprinting" in the Japanese Journal of Physiology, available at http://www.ncbi.nlm.nih.gov/sites/entrez?Db=pubmed&Cmd=ShowDetailView&TermToSearch=12139778&ordinalpos=4&itool=EntrezSystem2.PEntrez.Pubmed.Pubmed_ResultsPanel.Pubmed_RVDocSum, the contents of which are hereby incorporated by reference.

Accordingly, Applicants have discovered that the Arginine compound according to the first implementation, when ingested, provides enhanced Nitric Oxide (NO—) production while providing improved vasodilation effects over single administration of Arginine, the single administration of Nitrates, or the single administration of Nitrites. Improved vasodilation may, in turn, provide better circulation and distribution of Arginine in the body. Absorption may be improved since Amino Acid salts with inorganic acids are much more water soluble than single administration Amino Acids. Applicants have also discovered that the vasodilating effect of Arginine Nitrate manifests faster than that of single-administration Arginine, and as fast as any nitrate, since the $NO_3$— group of the salt requires minimal conversion to yield Nitric Oxide. Additionally a much lesser dose may be required for vasodilation to take place, compared to the single administration of Arginine. Likewise, the development of tolerance to the nitrate component of the molecule may be prevented with the presence of Arginine. Arginine Nitrate may promote vasodilation through production of Nitric Oxide by two different pathways, the Arginine citrullization pathway and the nitrate reduction pathway. Arginine Nitrate may likewise be more water soluble than single administration Arginine.

Accordingly, Applicants have discovered that the Citrulline compound according to the second implementation, when ingested, provides enhanced Nitric Oxide (NO—) production while providing improved vasodilation effects over single administration of Citrulline, the single administration of Nitrates, or the single administration of Nitrites. Improved vasodilation may, in turn, provide better circulation and distribution of Citrulline in the body. Absorption may be improved since Amino Acid salts with inorganic acids are much more water soluble than single administration Amino Acids. Additionally a much lesser dose may be required for vasodilation to take place, compared to the single administration of Citrulline or nitrates. Citrulline Nitrate is likewise more water soluble than single administration Citrulline.

Accordingly, Applicants have discovered that the Creatine compound according to the third implementation, when ingested, provides enhanced Nitric Oxide (NO—) production while providing improved vasodilation effects over single administration of Creatine, the single administration of Nitrates, or the single administration of Nitrites. Improved vasodilation may, in turn, provide better circulation and distribution of Creatine in the body. Absorption may be improved since Amino Acid salts with inorganic acids are much more water soluble than single administration Amino Acids. Additionally a much lesser dose may be required for vasodilation to take place, compared to the single administration of nitrates.

Enhancing a molecule's solubility can enhance it's bioavailability, rate of absorption by the GI tract, and as a result, it's concentration in the muscle tissue and it's effectiveness. As we have established, the nitrate salts of creatine and other molecules are exceptionally more soluble that their counterparts. Recent studies on creatine nitrate show 1100% improved solubility over creatine monohydrate.

Study 1: Intrinsic Dissolution Profiles of Creatine Nitrate, Creatine Monohydrate and Buffered Creatine Objective: The objective of this study was to determine the dissolution characteristics of three different forms of commercially available creatine including creatine nitrate (CN), creatine monohydrate (CM) and buffered creatine (BC) under different temperature and pH. Methods: Intrinsic dissolution studies were carried out at 37 °C and room temperature in pH 2.5 and 7.4 buffer using modified Wood's apparatus. CN, CM and BC samples (~0.5 g) were compressed in the dies with constant surface area of 1.21 cm2 using a Carver press at 2000 psi with a dwell time of 10 sec. These dies were placed in the USP dissolution apparatus (type II) containing 140 ml of dissolution media, with paddle speed of 50 rpm. Dissolution medium were collected at definite time intervals over a period of 3 hours for CN and 7 hours for both CM and BC and analyzed for creatine using a validated HPLC method. Results: A plot of the amount of creatine dissolved (mg)/surface area (cm2) versus time gives the slope (k') which is directly proportional to the dissolution rate constant. The k' (mg/cm2 hr) values for CN, CM and BC in pH 2.5 buffer at room temperature were 293.0±3.48, 59.1±2.06 and 71.1±0.59. At 37 °C these k' (mg/cm2 hr) values were 327.3±2.66, 97.9±0.88 and 117.9±1.12, respectively. In pH 7.4 buffer, the k' (mg/cm2 hr) values for CN, CM and BC were 278.9±14.6, 52.1±0.22 and 50.6±0.95 at room temperature and 319.5±14.3, 86.0±5.05 and 96.9±9.28 at 37 °C, respectively. Conclusions: The dissolution rates of all three creatine forms were higher at 37 °C as compared to at room temperature. CM and BC showed a higher dissolution rate at pH 2.5 than that at pH 7.4, irrespective of temperature. However, the dissolution rate of CN was not affected by the pH of the dissolution media. Comparison of the dissolution profiles for these three creatine forms clearly indicated that CN has the higher intrinsic dissolution rate constant as compared to CM and BC irrespective of temperature and pH of the dissolution media. Results of this study further predict a better bioavailability of CN as compared to CM and BC.

Study 2: Chemical Stability of Creatine Nitrate, Creatine Monohydrate and Buffered Creatine in Solution Objective: The objective of this study was to determine the chemical stability of creatine nitrate (CN), creatine monohydrate (CM) and buffered creatine (BC) under two different storage conditions (37 °C in pH 2.5 buffer and 40 °C in pH 6.8 buffer). Methods: A known concentration (~10 mg/ml) of CN, CM and BC were prepared in both pH 2.5 and pH 6.8 buffer and stored in stability chambers in screw capped bottles at 37 °C and 40 °C, respectively. Samples were collected at predetermined time points and analyzed for creatine and degradation products if any, using a validated HPLC method. Changes in the pH, clarity and color of the samples were also determined. The order of degradation and rate constant were determined by graphical method. Results: The degradation rate constants (k) for CN, CM and BC at 37 °C in pH 2.5 buffer were 0.075±0.001, 0.119±0.011 and 0.108±0.002 (day-1) while that at 40 °C in pH 6.8 buffer were 0.115±0.001, 0.015±0.001 and 0.013±0.002 (day-1), respectively. The pH of CN samples at 40 °C in pH 6.8 buffer changed from 2.83±0.01 to 4.31±0.01 within a period of 12 days. The pH changes noticed at 37 °C in pH 2.5 buffer samples over the same period of time for CM, and BC were 3.08±0.01 to 4.12±0.01 and 3.11±0.01 and 4.16±0.01, respectively. No significant change in pH was observed for the rest of the samples. No change in the color and the clarity was noticed over 12 days. Conclusions: All the creatine samples followed first order degradation kinetics under both these experimental conditions. The k value for CN was found to be higher at 40 °C in pH 6.8 buffer as compared to at 37 °C in pH 2.5 buffer. However, both CM and BC showed a faster rate of degradation at 37 °C in pH 2.5 buffer than at 40 °C in pH 6.8 buffer. The major degradation product detected was creatinine. For CN the increase in pH was higher at 40 °C in pH 6.8 buffer as compared to 37 °C in pH 2.5 buffer. However, opposite effect was noticed for both CM and BC.

Study 3: Equilibrium Solubilty Studies of Creatine Nitrate, Creatine Monohydrate and Buffered Creatine Ambrish Pandit1, Pinal Mistry1, Pat Dib2, Alexander Nikolaidis3 Alekha K. Dash1

Department of Pharmacy Sciences, Creighton University, Omaha, NE 68178. Department of Physiological Science UCLA. Aristotle University Of Thessaloniki.

Objective: The objective of this study was to determine the equilibrium solubility of creatine nitrate (CN), creatine monohydrate (CM) and buffered creatine (BC) in water at room temperature as well as in pH 2.5 buffer at room temperature and 37 °C. Methods: Excess amount of sample was added to the appropriate solvent and temperature was maintained and agitated at 150 rpm. The supernatant was collected after centrifugation at 24, 48, 72 hours till equilibration and analyzed by a HPLC method. Equilibration was confirmed when the solubility values of two consecutive time points were identical. The pH of the solution was monitored and Differential scanning calorimetry (DSC) thermograms of the solid samples before solubility and of the lyophilized sample after solubility studies were compared. Results: The equilibrium solubility of CN, CM and BC in water at room temperature was reached in 44 hours, and was 210.3±4.82 mg/ml, 19.1±0.40 mg/ml and 19.2±0.55 mg/ml, respectively. However, solubility for CN, CM and BC in pH 2.5 buffer at room temperature was 208.2±6.01 mg/ml, 23.8±0.33 mg/ml and 21.2±0.09 mg/ml and achieved within 72 hours for CN and in 48 hours for CM and BC samples, respectively. At 37 °C and in pH 2.5 buffer, the equilibrium solubility was reached within 24 hours for all samples and was 325.9±6.10, 31.5±0.71 and 32.6±0.67 for CN, CM, and BC. The pH of solutions of CN, CM and BC in water at room temperature was 0.44±0.04, 8.24±0.14 and 10.03±0.02 respectively. However, these values in pH 2.5 buffer at room temperature were 1.31±0.02, 3.44±0.02 and 3.68±0.01 and at 37 °C this was 1.13±0.07, 3.86±0.47 and 4.42±0.05, respectively. DSC thermograms of the original samples and lyophilized samples were identical. Conclusions: The solubility of creatine nitrate was around 10 fold higher than that of CM or BC under these experimental conditions studied, where as no significant difference in the solubility of CM and BC were noticed. There was an increase in solubility of each of the creatine forms in pH 2.5 at a higher temperature. DSC analysis confirmed that no phase change was noticed during these solubility studies.

The effectiveness of creatine for increasing athletic performance and improving body composition and muscle anabolism and performance is very well established. Such is also the case for BCAAs (leucine, isoleucine, and valine), taurine and carnitine. It is also well established that for these molecules to have these effects, like all drugs, they must reach the site of action, i.e. the muscle.

Creatine Nitrate & the Athlete

Creatine Nitrate excels beyond its superior solubility, stability, and dissolution. That's because Creatine Nitrate overcomes two primary drawbacks of creatine monohydrate. First, creatine monohydrate results in extreme intra and extracellular water and sodium retention. The intracellular water retention is favorable. Cosmetically speaking however, the extracellular water retention is an unfavorable effect, as an athlete's muscles develop a smooth, soft, and bloated appearance. Second and most importantly, the extreme extracellular water retention may restrict muscle growth. Functionally speaking, the extracellular water retention may push back against muscle cells that are attempting to expand in size.

Creatine Nitrate expels excess extracellular water and sodium retention, while simultaneously hydrating and supersaturating muscle cells with creatine. This offers a HUGE benefit to athletes, encouraging muscle cells to expand in size without resistance from extracellular fluid. In addition, athletes using Creatine Nitrate may achieve a leaner, drier, and harder look to their muscle tissue; a stark contrast to the puffy and bloated look created by creatine monohydrate. Creatine Nitrate however is more than "Creatine Nitrate," as the nitrate component offers tremendous functional advantages to athletes.

Nitrates provide substantial benefits to athletes and bodybuilders, as supported by clinical research. Nitrates are organic anions naturally occurring in the human diet, with close to 80% of dietary nitrates found in vegetables. Fruits and processed meats represent additional sources of nitrates in the human diet. In fact, researchers at Michigan State University have suggested nitrates may be nutritious (13). So what benefit does supplementation with nitrates offer to athletes?

Today, nitric oxide and pre-workout nitric oxide performance enhancing formulas have grown in popularity. Nitric oxide formulas are used to increase muscular "pumps," vasodilation, and nutrient transport to the muscle to assist in greater aerobic performance and recovery. However, most formulas utilize the amino acid L-arginine, a precursor to nitric oxide, as their base. Recently, L-arginine has been proven to be ineffective for elevating nitric oxide levels. L-arginine has also been proven ineffective at enhancing athletic performance (9,10,11). Yet L-arginine is present in nearly every single nitric oxide formula on the market. Contrary to popular belief, most of the "pump" feeling experienced by trainees is derived from an insulin increase following L-arginine supplementation (1).

As recent clinical research confirms, the reduction of inorganic nitrate ($NO_3^-$) and nitrite ($NO_2^-$) in vivo results in nitric oxide production. Not only does nitrate generate nitric oxide, but nitrate and nitrite are inert end-products of nitric oxide oxidation. That is, nitrate converts into nitric oxide, and once oxidized, nitric oxide is recycled back into nitrate, which then has the potential to convert into nitric oxide once again. And the cycle continues to repeat itself. This creates an exciting alternative to nitric oxide production, and carries profound implications for the bodybuilding community.

A critical problem with nitric oxide is the short lifespan it has in the body. In just a few seconds, the nitric oxide molecule can be metabolized, and the athlete loses any benefit he/she may have received. A pump however must be sustained for several minutes, if not hours, in order to result in those biochemical conditions required to stimulate muscle hypertrophy. And nitrates are capable of elevating nitric oxide production for up to 8 hours.

Thus the use of nitrates represents an important alternative to the classical L-arginine-NO-synthase pathway (2) so commonly attempted in various sports supplement formulations.

The efficacy of nitrates in athletic performance is overwhelming in the clinical research. Nitrate consumption significantly enhances nitric oxide production, resulting in vasodilation, improved nutrient absorption, increased athletic performance (3), and improved energetic function in working muscles during exercise (12). For example, during low and moderate intensity exercise by humans, supplementation with nitrates has been reported to reduce the amount of oxygen required. During high intensity athletic exercise, nitrate supplementation enhances tolerance to high intensity training, effectively extending the "time to exhaustion" (4).

Organic nitrates also function as permeation enhancers. This is beneficial because enhanced permeation increases intestinal absorption of all nutrients coingested. This may allow for a superior quantity of anabolic nutrients to be absorbed and taken up into muscle cells, assisting athletes with the growth and repair of muscle tissue. Nitrates are even able to allow absorption of large macromolecules such as insulin (5,6,7).

For decades, the pharmaceutical industry has used nitrates to induce direct and rapid vasodilation. And today, clinical research is proving that nitrates may produce beneficial effects on blood pressure and cardiovascular health (8). In fact, a recent clinical study investigated the effects of 5 times the amount of nitrates (1,316 mg per day for a 70 kg adult) currently recommended by the World Health Organization (259 mg per day for a 70 kg adult) and showed no adverse health or safety effects. The study results revealed an average reduction in diastolic blood pressure by 4.5 mmHg. Effects on systolic blood pressure were not observed (14, 15).

Nitrates themselves offer many benefits to athletes. Combined with the clinical research behind creatine supporting creatine's positive benefits to athletes, Creatine Nitrate is the first creatine to solve to the solubility, stability, and dissolution challenges while simultaneously providing up to 8 hours of powerful vasodilation that workout enthusiasts demand!

REFERENCES

The following references are hereby incorporated herein by reference.

1. Glucose- and arginine-induced insulin secretion by human pancreatic B-cells: the role of HERG K+ channels in firing and release
2. Does N O metabolism play a role in the effects of vegetables in health? Nitric oxide formation via the reduction of nitrites and nitrates. Dina Ralt*Gertner Institute for Epidemiology and Health Policy Research, Tel Hashomer, Israel
3. Larsen F J, Weitzberg E, Lundberg J O, Ekblom B. Effects of dietary nitrate on oxygen cost during exercise. Acta Physiol (Oxf). 2007 September; 191(1):59-66. Epub 2007 Jul. 17.
4. Stephen J. Bailey, 1 Paul Winyard, 2 Anni Vanhatalo, 1 Jamie R. Blackwell, 1 Fred J. DiMenna, 1 Daryl P. Wilkerson, 1 Joanna Tarr, 2 Nigel Benjamin, 2 and Andrew M. Jones 1. Dietary nitrate supplementation reduces the 02 cost of low-intensity exercise and enhances tolerance to high-intensity exercise in humans. 1School of Sport and Health Sciences and; 2Peninsula College of Medicine and Dentistry, University of Exeter, Exeter, United Kingdom
5. Fetih G, Habib F, Katsumi H, Okada N, Fujita T, Attia M, Yamamoto A. Excellent absorption enhancing characteristics of NO donors for improving the intestinal absorption of poorly absorbable compound compared with conventional absorption enhancers.
6. Koichi Takahashia, *, Nanako Numataa, Natsumi Kinoshitaa, Naoki Utoguchib, Tadanori Mayumic, Nobuyasu Mizunoa. Characterization of the influence of nitric oxide donors on intestinal absorption of macromolecules. International Journal of Pharmaceutics 286 (2004) 89-97
7. Fetih G, Habib F, Okada N, Fujita T, Attia M, Yamamoto A. Nitric oxide donors can enhance the intestinal transport and absorption of insulin and [Asu(1,7)]-eel calcitonin in rats.
8. Supatra Porasuphatanaa, Pei Tsaib, Gerald M. Rosenb. The generation of free radicals by nitric oxide synthase. Comparative Biochemistry and Physiology Part C 134 (2003) 281-289 1532-0456/03/$—see front matter_2002 Elsevier Science Inc. All rights reserved. PII: 51532-0456Ž02.00271-5 Review.
9. Olek R A et al. A single oral intake of arginine does not affect performance during repeated Wingate anaerobic test. J Sports Med Phys Fitness. 2010 March; 50(1): 52-6.
10. Liu T H, Wu C L, Chiang C W, Lo Y W, Tseng H F, Chang C K. No effect of shortterm arginine supplementation on nitric oxide production, metabolism and performance in intermittent exercise in athletes. J Nutr Biochem. 2008 Aug. 15. [Epub ahead of print]
11. Bescós R, Gonzalez-Haro C, Pujol P, Drobnic F, Alonso E, Santolaria M L, Ruiz O, Esteve M, Galilea P. Effects of dietary L-arginine intake on cardiorespiratory and metabolic adaptation in athletes. Int J Sport Nutr Exerc Metab. 2009 August; 19(4):355-65.
12. Larsen F J, Weitzberg E, Lundberg J O, Ekblom B. Dietary nitrate reduces maximal oxygen consumption while maintaining work performance in maximal exercise. Free Radic Biol Med. 2010 Jan. 15; 48(2):342-7. Epub 2009 Nov. 12.
13. American Journal of Clinical Nutrition, doi:10.3945/ajcn.2008.27131
14. Tanja Sobko, Claude Marcus, Mirco Govoni, Shigeru Kamiya. "Dietary nitrate in Japanese traditional foods lowers diastolic blood pressure in healthy volunteers." Nitric Oxide Volume 22, Issue 2, Pages 136-140
15. http://www.foodnavigator.com/Product-Categories/Preservativesand-acidulants/Dietary-nitrates-maybe-beneficial-for-heart-health-Study/?utm_source=Newsletter_Product&utm_medium=email&utm_campaign=Newsletter%2BProduct Accordingly, Applicants have discovered that the Glutamine compound according to the fourth implementation, when ingested, counters the Nitric Oxide (NO—) inhibiting characteristics of Glutamine. Absorption of Glutamine may be improved since Amino Acid salts with inorganic acids are much more water soluble than single administration Amino Acids. Additionally a much lesser dose may be required for vasodilation to take place, compared to the single administration of nitrates. Glutamine Nitrate may likewise be more water soluble than single administration Glutamine.

Accordingly, Applicants have discovered that the Leucine compound according to the fifth implementation, when ingested, provides enhanced Nitric Oxide (NO—) production while providing improved vasodilation effects over single administration of Leucine, the single administration of Nitrates, or the single administration of Nitrites. Improved vasodilation may, in turn, provide better circulation and distribution of Leucine in the body. Absorption may be improved since Amino Acid salts with inorganic acids are much more water soluble than single administration Amino Acids. Additionally a much lesser dose may be required for vasodilation to take place, compared to the single administration of nitrates. Leucine Nitrate is likewise more water soluble than single administration Leucine.

Accordingly, Applicants have discovered that the Norvaline compound according to the sixth implementation, when ingested, promotes vasodilation through the inhibition of arginase, while promoting Nitric Oxide formation via the nitrate mechanism. Improved vasodilation may, in turn, provide better circulation and distribution of Norvaline in the body. Absorption may be improved since Amino Acid salts with inorganic acids are much more water soluble than single administration Amino Acids. Additionally a much lesser dose may be required for vasodilation to take place, compared to the single administration of nitrates. Norvaline Nitrate may likewise be more water soluble than single administration Norvaline.

Accordingly, Applicants have discovered that the Ornithine compound according to the seventh implementation, when ingested, provides an additional vasodilation mechanism, reducing the amount of Ornithine needed and the amount of time needed for the vasodilating properties to manifest. Improved vasodilation may, in turn, provide better circulation and distribution of Ornithine in the body. Absorption may be improved since Amino Acid salts with inorganic acids are much more water soluble than single administration Amino Acids. Applicants have also discovered that Ornithine Nitrate begins acting as fast as any other nitrate, since the $NO_3$— group of the salt requires minimal conversion to yield Nitric Oxide. Additionally, a much lesser dose may be required for vasodilation to take place, compared to the single administration of nitrates. Ornithine Nitrate may likewise be more water soluble than single administration Ornithine.

Accordingly, Applicants have discovered that the Histidine compound according to the eighth implementation, when ingested, provides a vasodilation mechanism. Vasodilation may, in turn, provide better circulation and distribution of Histidine in the body. Applicants have likewise discovered that the Histidine compound according to the ninth implementation, when ingested, promotes carnosine production, thus increasing muscle power, endurance and recuperation. Absorption may be improved since Amino Acid salts with inorganic acids are much more water soluble than single administration Amino Acids. Applicants have also discovered that Histidine Nitrate begins acting as fast as any other nitrate, since the $NO_3$— group of the salt requires minimal conversion to yield Nitric Oxide. Additionally, a much lesser dose may be required for vasodilation to take place, compared to the single administration of nitrates. Histidine Nitrate may likewise be more water soluble than single administration Histidine.

Accordingly, Applicants have discovered that the Beta Alanine compound according to the ninth implementation, when ingested, provides vasodilation. Vasodilation may, in turn, provide better circulation and distribution of Beta Alanine in the body. Applicants have likewise discovered that the Beta Alanine compound according to the tenth implementation, when ingested, promotes carnosine production, thus increasing muscle power, endurance and recuperation. Absorption may be improved since Amino Acid salts with inorganic acids are much more water soluble than single administration Amino Acids. Applicants have also discovered that Beta Alanine Nitrate begins acting as fast as any other nitrate, since the $NO_3$— group of the salt requires minimal conversion to yield Nitric Oxide. Additionally, a much lesser dose may be required for vasodilation to take place, compared to the single administration of nitrates. Beta Alanine Nitrate may likewise be more water soluble than single administration Beta Alanine.

Accordingly, Applicants have discovered that the Agmatine compound according to the eighth implementation, when ingested, counteracts the Nitric Oxide inhibiting effect of single administration Agmatine. Absorption may be improved since Amino Acid salts with inorganic acids are much more water soluble than single administration Amino Acids. Applicants have also discovered that Agmatine Nitrate begins acting as fast as any other nitrate, since the $NO_3$— group of the salt requires minimal conversion to yield Nitric Oxide. Agmatine Nitrate may likewise be more water soluble than single administration Agmatine.

Accordingly, Applicants have discovered that not only do the foregoing amino acid nitrate or nitrite compounds provide the effects discussed above, but that Amino Acid Compositions (amino acids mixed with independent sources of nitrates and/or nitrites) enhance bioavailability, absorption, vasodilation, water solubility, distribution to muscles, and the like of certain Amino Acids, as well as prevent Nitrate tolerance and counter Nitric Oxide inhibiting effects of certain Amino Acids.

As demonstrated by Anjali Pradhan and Juan Vera, "Effect of Anions on the Solubility of Zwitterionic Amino Acids", Journal of Chemical and Engineering data, Vol 45, 140-143 (2000) (which is hereby incorporated herein by reference), the co-existence of the nitrate ion can enhance the solubility of various amino acids by 300-400%. Although the change in solubility is significantly lower than that of the case of a salt with a nitrate, it is enough to make a difference in absorption in-vivo.

Furthermore, the nitrate ion enhances absorption of compounds by the intestine. Nitrates can increase bioavailability. As nitric oxide donors, nitrates increase vasodilation and blood flow and, because blood is the carrier of the nutrients to cells, increase intestinal absorption of nutrients. See for example, the following references which are hereby incorporated herein by reference: Takahashi K et al. "Characterization of the influence of nitric oxide donors on intestinal absorption of macromolecules." Int J Pharm 2004; 286:89-97; Fetih G et al. "Nitric oxide donors can enhance the intestinal transport and absorption of insulin and [Asu(1, 7)]-eel calcitonin in rats." J Control Release 2005; 106:287-97; Fetih G et al. "Excellent absorption enhancing characteristics of NO donors for improving the intestinal absorption of poorly absorbable compound compared with conventional absorption enhancers." Drug Metab Pharmacokinet 2006; 21:222-9; and Mitchell, G. E., Little, C. O., Jr. & Greathouse, T. R. (1964). "Influence of nitrate and nitrite, on carotene disappearance from the rat intestine." Life Sci. 4, 385.

Also, the nitrate ion can cause vasodilatation after reduction to nitrite and then nitric oxide, improve blood circulation, to the muscles and thus distribution of these compounds to the muscle, as well as oxygen distribution to the muscles. Muscle oxygen is needed to provide energy which is needed for all muscle anabolic actions to take place as well as for the active transport of above nutrients via the cell membrane. See the following references which are hereby incorporated herein by reference—Bailey, Stephen G. et al., "Dietary nitrate supplementation reduces the O2 cost of low-intensity exercise and enhances tolerance to high-intensity exercise in humans", PresS. J Appl Physiol (Aug. 6, 2009) and Bailey, Stephen G. et al., "Dietary nitrate supplementation enhances muscle contractile efficiency during knee-extensor exercise in humans", J Appl Physiol 109:135-148, 2010).

In these same references it is also very well described nitrate's positive effect on athletic endurance and muscle strength. Oxygen is needed by the body to produce energy which by itself is needed for all the metabolic processes in the body, including those that Compositions of the present disclosure are involved in. Thus co-administration of nitrate ion with Compositions of the present disclosure furthermore increases their distribution to the muscle and their effectiveness.

Therefore, not only does the binding of nitrate salt with Compounds improve their bioavalability, absorption and effectiveness, but also the co-administration of nitrate through another nitrate salt, acid or a natural source of nitrate in a Composition of the present disclosure shall have similar effects, albeit lower than in the case of nitrate bonded with the molecule.

Via all the above mechanisms, concomitant nitrate or nitrite administration in a composition with an amino acid can substantially increase the concentration of an amino acid in the target muscles (e.g., Neuron cells for the congitive enhancement properties of Phenylalanine, Carnitine, Glycine, and Tyrosine, and Muscle cells for the performance enhancing properties of Agmatine Arginine, Beta Alanine, Citrulline, Creatine, Glutamine, L-Histidine, Isoleucine, Leucine, Norvaline, Ornithine and Taurine). In the case of Creatine, this is further enhanced by the nitrate's ability to preserve muscle Creatine loads.

Therefore, concomitant nitrate or nitrite administration in a composition with an amino acid (just as with amino acid nitrate or nitrite compounds discussed previously) can improve mental focus, cognitive function, athletic and muscle performance, endurance, and strength, and produces much greater synergistic results than the use of only an amino acid alone or a nitrate and a nitrite alone.

We claim:

1. A solid supplement composition comprising:
at least one non-ester nitrate compound; and
at least one isolated amino acid compound;
wherein the at least one isolated amino acid compound is creatine;
wherein the at least one isolated amino acid compound is a separate compound than the at least one non-ester nitrate compound; and
wherein the solid supplement composition comprises an amount of nitrate ion ($NO_3^-$) that is at least 1 mg.

2. The composition of claim 1, wherein the solid supplement composition is in the form of powder.

3. The composition of claim 1, wherein the solid supplement composition is in the form of gel.

4. The composition of claim 1, wherein the solid supplement composition is in the form of powder and the amount of nitrate ion ($NO_3^-$) is at least 7 mg.

5. The composition of claim 1, wherein the solid supplement composition is in the form of gel and the amount of nitrate ion ($NO_3^-$) is at least 5 mg.

6. The composition of claim 1, wherein the solid supplement composition is in the form of powder and the amount of nitrate ion ($NO_3^-$) is at least 160 mg.

7. The composition of claim 1, wherein the solid supplement composition is in the form of powder, the amount of nitrate ion ($NO_3^-$) is at least 7 mg, and the solid supplement composition further comprises beetroot, spinach, carrot, broccoli, and mushroom.

8. The composition of claim 1, wherein the solid supplement composition is in the form of powder, the amount of nitrate ion ($NO_3^-$) is at least 160 mg, and the solid supplement composition further comprises beetroot, spinach, carrot, broccoli, and mushroom.

9. The composition of claim 1, wherein the solid supplement composition comprises at least one component that is ion-exchange resin-based.

10. The composition of claim 1, wherein the solid supplement composition is in the form of powder or gel and the solid supplement composition further comprises an antioxidant.

11. The composition of claim 1, wherein the solid supplement composition is in the form of powder and the solid supplement composition further comprises citric acid, wherein the citric acid is from a separate source than the isolated amino acid compound and the at least one non-ester nitrate compound.

12. The composition of claim 1, wherein the solid supplement composition is in the form of powder or gel, and the solid supplement composition further comprises three or more of the following: beetroot, spinach, rocket, carrot, broccoli, cabbage, and mushroom.

13. The composition of claim 1, wherein the solid supplement composition is in the form of powder or gel and the solid supplement composition further comprises four or more of the following:
beetroot, spinach, rocket, carrot, broccoli, cabbage, and mushroom.

14. The composition of claim 1, wherein the solid supplement composition is in the form of powder or gel and the solid supplement composition further comprises five or more of the following:
beetroot, spinach, rocket, carrot, broccoli, cabbage, and mushroom.

15. The composition of claim 1, wherein the solid supplement composition is in the form of powder or gel and the solid supplement composition further comprises a botanical nitrate source, a vegetable nitrate source, and an antioxidant.

16. The composition of claim 1, wherein the solid supplement composition is in the form of powder or gel and wherein the solid supplement composition further comprises beetroot and an antioxidant.

17. The composition of claim 1, wherein the solid supplement composition is in the form of powder or gel, and wherein the solid supplement composition further comprises at least one isolated amino acid compound selected from: aspartic acid, proline, glycine, valine, agmatine, norvaline, ornithine, and arginine.

18. The composition of claim 1, wherein the solid supplement composition is in the form of powder or gel, and wherein the amount of nitrate ion ($NO_3^-$) is at least 7 mg, and wherein the solid supplement composition further comprises at least one isolated amino acid compound selected from: aspartic acid, proline, glycine, valine, agmatine, norvaline, ornithine, and arginine.

19. The composition of claim 1, wherein the solid supplement composition is in the form of powder or gel, and wherein the solid supplement composition further comprises at least two isolated amino acid compounds selected from: aspartic acid, proline, glycine, valine, agmatine, norvaline, ornithine, and arginine.

20. The composition of claim 1, wherein the solid supplement composition is in the form of powder or gel, and wherein the amount of nitrate ion ($NO_3^-$) is at least 7 mg, and wherein the solid supplement composition further comprises at least two isolated amino acid compounds selected from: aspartic acid, proline, glycine, valine, agmatine, norvaline, ornithine, and arginine.

21. The composition of claim 1, wherein the solid supplement composition is in the form of powder or gel, and wherein the solid supplement composition further comprises at least three isolated amino acid compounds selected from: aspartic acid, proline, glycine, valine, agmatine, norvaline, ornithine, and arginine.

22. The composition of claim 1, wherein the solid supplement composition is in the form of powder, the amount of nitrate ion ($NO_3^-$) is at least 7 mg, and the solid supplement composition further comprises at least three isolated amino acid compounds selected from: aspartic acid, proline, glycine, valine, agmatine, norvaline, ornithine, and arginine.

23. The composition of claim 1, wherein the solid supplement composition is in the form of powder or gel, and wherein the solid supplement composition further comprises at least four isolated amino acid compounds selected from: aspartic acid, proline, glycine, valine, agmatine, norvaline, ornithine, and arginine.

24. The composition of claim 1, wherein the solid supplement composition is in the form of powder, the amount of nitrate ion ($NO_3^-$) is at least 7 mg, and the solid supplement composition further comprises at least four isolated amino acid compounds selected from: aspartic acid, proline, glycine, valine, agmatine, norvaline, ornithine, and arginine.

25. The composition of claim 1, wherein the solid supplement composition further comprises an isolated amino acid compound that is glycine.

26. The composition of claim 1, wherein the composition is in the form of powder, the amount of nitrate ion ($NO_3^-$) is at least 7 mg, and the solid supplement composition further comprises an isolated amino acid compound that is glycine.

27. The composition of claim 1, wherein the composition is in the form of powder, the amount of nitrate ion ($NO_3^-$) is at least 7 mg, and the solid supplement composition further comprises at least about 200 mg of an isolated amino acid compound that is glycine.

28. The composition of claim 1, wherein the solid supplement composition further comprises an isolated amino acid compound that is aspartic acid.

29. The composition of claim 1, wherein the composition is in the form of powder, the amount of nitrate ion ($NO_3^-$) is at least 7 mg, and further comprises an isolated amino acid compound that is aspartic acid.

30. The composition of claim 1, wherein the composition is in the form of powder, the amount of nitrate ion ($NO_3^-$) is at least 7 mg, and the composition further comprises beetroot, spinach, broccoli, and isolated amino acid compounds that are aspartic acid, proline, glycine, valine, and arginine.

* * * * *